US010357457B2

(12) United States Patent
Gieseler et al.

(10) Patent No.: US 10,357,457 B2
(45) Date of Patent: Jul. 23, 2019

(54) TARGETED LIPID-DRUG FORMULATIONS FOR DELIVERY OF DRUGS TO MYELOID AND LYMPHOID IMMUNE CELLS

(71) Applicant: RODOS BioTarget GmbH, Hanover (DE)

(72) Inventors: Robert K. Gieseler, Essen (DE); Guido Marquitan, Altendiez (DE); Michael J. Scolaro, Sun City, AZ (US); Sean M. Sullivan, Gainesville, FL (US)

(73) Assignee: Rodos BioTarget GmbH, Hannover (DE)

( * ) Notice: Subject to any disclaimer, the term of this patent is extended or adjusted under 35 U.S.C. 154(b) by 0 days.

(21) Appl. No.: 15/154,097

(22) Filed: May 13, 2016

(65) Prior Publication Data
US 2016/0324779 A1 Nov. 10, 2016

Related U.S. Application Data

(63) Continuation of application No. 14/193,498, filed on Feb. 28, 2014, now abandoned, which is a continuation of application No. 10/943,758, filed on Sep. 17, 2004, now abandoned.

(60) Provisional application No. 60/567,376, filed on Apr. 30, 2004, provisional application No. 60/503,769, filed on Sep. 17, 2003.

(51) Int. Cl.
*A61K 39/00* (2006.01)
*A61K 9/127* (2006.01)
*A61K 36/185* (2006.01)
*A61K 38/16* (2006.01)
*A61K 39/085* (2006.01)
*A61K 39/395* (2006.01)
*A61K 47/69* (2017.01)

(52) U.S. Cl.
CPC ............ *A61K 9/127* (2013.01); *A61K 36/185* (2013.01); *A61K 38/168* (2013.01); *A61K 39/085* (2013.01); *A61K 39/395* (2013.01); *A61K 39/3955* (2013.01); *A61K 47/6913* (2017.08)

(58) Field of Classification Search
None
See application file for complete search history.

(56) References Cited

U.S. PATENT DOCUMENTS

| 4,795,739 A * | 1/1989 | Lifson ..................... A61K 36/42 424/758 |
| 5,766,902 A | 6/1998 | Craig et al. |
| 7,357,930 B1 | 4/2008 | Bergeron et al. |
| 2003/0044407 A1 | 3/2003 | Chang et al. |
| 2004/0208921 A1 | 10/2004 | Ho et al. |

FOREIGN PATENT DOCUMENTS

| EP | 0 552 280 B1 | 6/1995 |
| JP | 6-504429 A | 5/1994 |
| JP | 2002-543162 A | 12/2002 |
| WO | WO 00/66173 A2 | 11/2000 |
| WO | WO 03/061602 A2 | 7/2003 |
| WO | WO 03/079757 A2 | 10/2003 |

OTHER PUBLICATIONS

McCoig et al., 1999, PNAS, vol. 96: 11482-11485.
Zelphati et al., (1993) "Inhibition of HIV-1 Replication in Cultured Cells With Antisense Oligonucleotides Encapsulated Immunolipsomes", Antisense Res Development 3:323-338.
Sapra et al., (2003; Medline Edate: Jun. 20, 2003), Ligand-Targeted Liposomal Anticancer Drugs, Prog. Lipid Res. 42:439-462.
Selvam et al., (1996) "Inhibition of HIV Replication by Immunoliposomal Antisense Oligonucleotide", Antiviral Res. 33:11-20.
Trumpfheller et al., (2003) "Cell Type Dependent Retention and Transmission of HIV-1 by DC-SIGN", International Immunology 15:289-298.
Jean-Paul Leonetti et al., Antibody-Targeted Liposomes Containing Oligodeoxyribonucleotides Complementary to Viral RNA Selectively Inhibit Viral Replication; Proc. Natl. Acad. Sci., Apr. 1990, pp. 2448-2451, vol. 87, Medical Sciences, USA.
Karin Renneisen et al., Inhibition of Expression of Human Immunodeficiency Virus-1 in vitro by Antibody-Targeted Liposomes Containing Antisense RNA to the Env Region; The Journal of Biological Chemistry, Sep. 1990, pp. 16337-16342, vol. 265, No. 27, USA.
Karoline W. Schjetne et al., A Mouse Ck-Specific T Cell Clone Indicates that DC-SIGN is an Efficient Target for Anitbody-Medicated Delivery of T Cells Epitopes for MHC Class II Presentation; International Immunology, 2002, pp. 1423-1430, vol. 14, No. 12, The Japanese Society for Immunology, Japan.

(Continued)

Primary Examiner — Amy E Juedes
(74) Attorney, Agent, or Firm — Crowell & Moring LLP

(57) ABSTRACT

A method of preferentially delivering an active agent to an immune cell, such as a myeloid progenitor cell, a dendritic cell, a monocyte, a macrophage or a T-lymphocyte, or other cell type restricted to a functional organ system or an anatomic entity, of a mammalian subject by administering a lipid-drug complex to the subject. The lipid-drug complex is comprised of an active agent, such as a drug, and an outer surface with a targeting ligand that binds a marker on the surface of the immune cell or other cell type that is infected with or susceptible to infection with an infectious agent. The other cell type that is infected with or susceptible to infection with an infectious agent may belong to a malignant tumor or a part of the immune system contributing to the development, maintenance, or exacerbation of an autoimmune disease or chronic inflammatory disease.

8 Claims, 6 Drawing Sheets
Specification includes a Sequence Listing.

(56) References Cited

OTHER PUBLICATIONS

Frederic Baribaud et al., Quantitative Expression and Virus Transmission Analysis of DC-SIGN on Monocyte-Derived Dendritic Cells; Journal of Virology, Sep. 2002, pp. 9135-9142, vol. 76, No. 18, American Society for Microbiology, USA.

Anneke Engering et al., The Dendritic Cell-Specific Adhesion Receptor DC-SIGN Internalizes Antigen for Presentation to T Cells; The Journal of Immunology, 2002, pp. 2118-2126, The American Association of Immunologists, USA.

Romila D. Charan et al., Isolation and Characterization of Myrianthus Holstii Lectin, a Potent HIV-1 Inhibitory Protein from the Plant Myrianthus Holstii; Journal of Natural Products, 2000, pp. 1170-1174, vol. 63, No. 8, American Chemical Society and American Society of Pharmacognosy, USA.

R. K. Gieseler et al., DC-SIGN-Specific Liposomal Targeting and Selective Intracellular Compound Delivery to Human Myeloid Dendritic Cells: Implications for HIV Diease; Scandinavian Journal of Immunology, 2004, pp. 415-424, vol. 59, Blackwell Publishing Ltd.

Lisa Scherer et al., Recent Applications of RNAi in Mammalian Systems; Current Parmaceutical Biotechnology. 2004, pp. 355-360, vol. 5, No. 4, Bentham Science Publishers Ltd.

Istvan Botos et al., Proteins that Bind High-Mannose Sugars of HIV Envelope; Progress in Biophysics and Molecular Biology; 2005, pp. 233-282, vol. 88, Elsevier.

Lee, et al. "Expression of DC-SIGN Allows for More Efficient Entry of Human and Simian Immunodeficiency Viruses via CD4 and a Coreceptor", Journal of Virology, Dec. 2001, p. 12028-12038, vol. 75, No. 24, (Eleven (11) pages).

Robichaud, et al. "Nuclear Factor of Activated T Cells is a Driving Force for Preferential Productive HIV-1 Infection of CD45RO-expressing CD4+ T Cells", The Journal of Biological Chemistry, 2002, The American Society for Biochemistry and Molecular Biology, Inc., vol. 277, No. 25, Issue of Jun. 28, pp. 23733-23741, (Nine (9) pages).

Charan et al., 2000, J. Nat. Prod., vol. 63 : 1170-1174.

Resino et al., "Naïve and memory $CD4^+$ T cells and T cell activation markers in HIV-1 infected children on HAART", Clin. Exp. Immunol., 2001: 125: 266-273 (Eight (8) pages).

\* cited by examiner

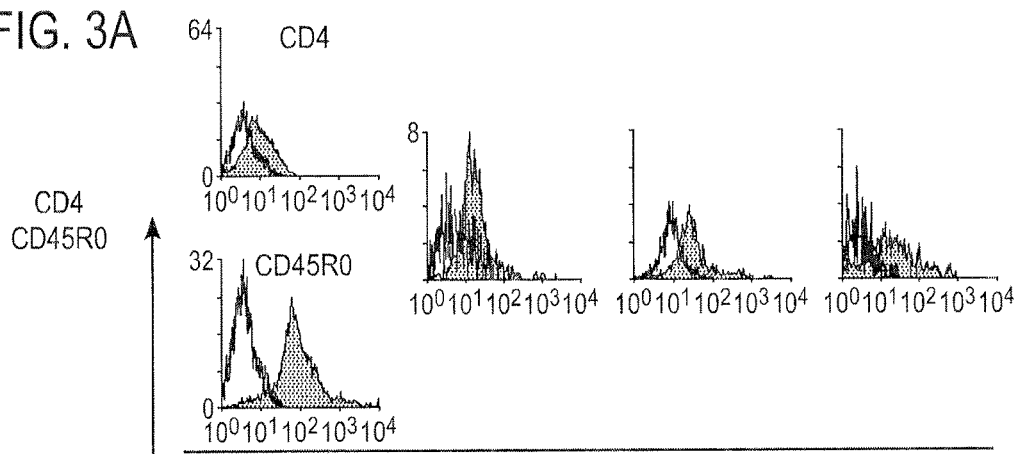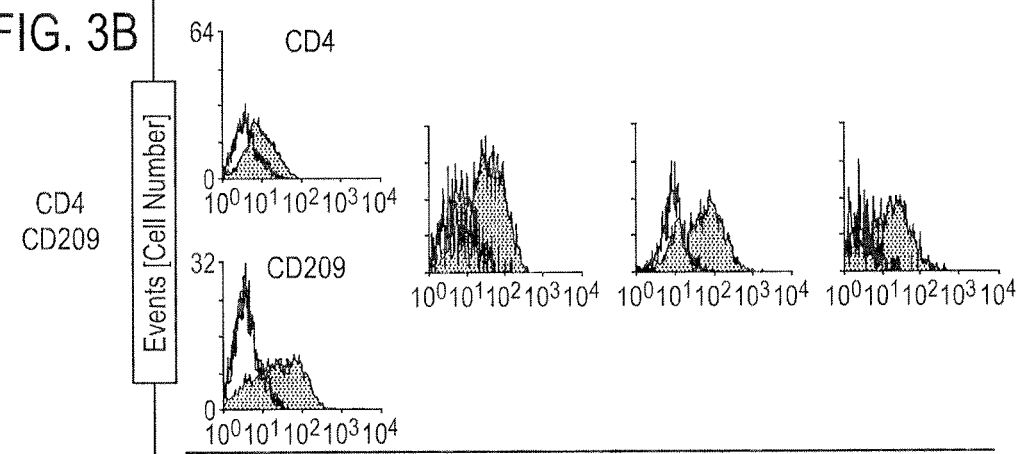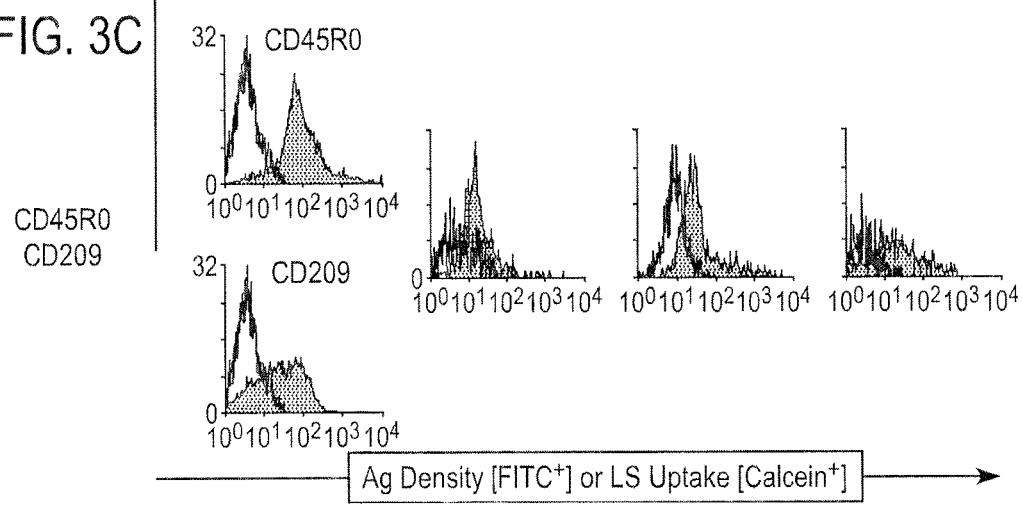

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
agtgggggga catcaagcag ccatgcaaat                                    30

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
tcatctggcc tggtgcaa                                                 18

<210> SEQ ID NO 3
<211> LENGTH: 28
<212> TYPE: DNA
<213> ORGANISM: Artificial Sequence
<220> FEATURE:
<223> OTHER INFORMATION: Primer; Labeled with 5-carboxyfluorescein

<400> SEQUENCE: 3
cagcttagag accatcaatg aggaagcg                                      28

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ggtgcaatag gccctgcat                                                19
```

TARGETED LIPID-DRUG FORMULATIONS FOR DELIVERY OF DRUGS TO MYELOID AND LYMPHOID IMMUNE CELLS

This Application is a continuation of U.S. patent application Ser. No. 14/193,498, filed Feb. 28, 2014, which is a continuation of U.S. patent application Ser. No. 10/943,758, filed Sep. 17, 2004, which claims priority under 35 U.S.C. 119 from U.S. provisional patent application No(s). 60/567,376, filed Apr. 30, 2004, and 60/503,769, filed Sep. 17, 2003, the entire disclosures of which are expressly incorporated by reference herein.

BACKGROUND OF THE INVENTION

1. Field of the Invention

The present invention relates to the medical arts, and in particular, to targeted liposomal drug delivery.

2. Discussion of the Related Art

Myeloid dendritic cells (My-DCs) belong to the most potent group of professional antigen-presenting cells, with the unique ability to induce primary cellular and humoral immune responses (reviewed in Banchereau J, Paczesny S, Blanco P, Bennett L, Pascual V, Fay J, Palucka A K, *Dendritic cells: controllers of the immune system and a new promise for immunotherapy*, Ann N.Y. Acad Sci 987:180-7 [2003]). These cells, within the lymphoid organs and structures, are also an important component of the HIV reservoir, together with other major sanctuary populations, i.e. follicular dendritic cells, macrophages, resting/memory T cells, and cells within the central nervous system. (E.g., Schrager L K, D'Souza M P, *Cellular and anatomical reservoirs of HIV-I in patients receiving potent antiretroviral combination therapy*, JAMA 280:67-71 [1998]). It is a key characteristic of reservoir cells that they are compromised and exploited, but not killed, by HIV, thus leading to a continuous infection of other immune and non-immune cells within an infected person. (Gieseler R K, Marquitan G, Scolaro M J, Cohen M D, *Lessons from history: dysfunctional APCs, inherent dangers of STI and an important goal, as yet unmet*, Trends Immunol. 2003; 24:11).

In-vitro generation of My-DCs has enabled comprehensive phenotypic and functional characterization of the My-DCs and the study of the ontogeny of these cells, which have been found to share with macrophages an early common myeloid progenitor (Gieseler R K, Röber R A, Kuhn R, Weber K, Osborn M, Peters J H, *Dendritic accessory cells derived from rat bone marrow precursors under chemically defined conditions in vitro belong to the myeloid lineage*, Eur J Cell Biol 1991; 54:171-81; Peters J H, Xu H, Ruppert J, Ostermeier D, Friedrichs D, Gieseler R K, *Signals required for differentiating dendritic cells from human monocytes in vitro*, Adv Exp Med Biol 1993; 329:275-80; Peters J H, Gieseler R, Thiele B, Steinbach F, *Dendritic cells: from ontogenetic orphans to myelomonocytic descendants*, Immunol Today 1996; 17:273-8; Gieseler R, Heise D, Soruri A, Schwartz P, Peters J H, *In-vitro differentiation of mature dendritic cells from human blood monocytes*, Dev Immunol 1998; 6:25-39).

The discovery of the My-DC-specific intercellular adhesion molecule 3-grabbing nonintegrin (DC-SIGN) in the year 2000 was a milestone of immunologic research: DC-SIGN, one of several C-type lectins, is both a distinctive key DC molecule and plays an essential role in the capture and migratory transport of HIV. Besides T-cell infection due to active virus production by My-DCs, interaction of HIV and DC-SIGN eventually enables My-DCs to infect in-trans cooperating T-helper cells. Also, variants of DC-SIGN are expressed by macrophages (another major HIV-1 reservoir), as well as by several mucosal and placental cell types (Soilleux, E J et al. *Constitutive and induced expression of DC-SIGN on dendritic cell and macrophage subpopulations in situ and in vitro*, J Leukoc Biol 71:445-57 [2002]; Geijtenbeek, T B H et al., *Marginal zone macrophages express a murine homologue of DC-SIGN that captures blood-borne antigens in vivo*, Blood 100:2908-16 [2002]; Soilleux E J et al., *Placental expression of DC-SIGN may mediate intrauterine vertical transmission of HIV*, J Pathol. 195(5):586-92 [2001]; Soilleux E J, Coleman N, *Transplacental transmission of HIV: a potential role for HIV binding lectins*, Int J Biochem Cell Biol.; 35(3):283-7 [2003]; Kammerer U et al., *Unique appearance of proliferating antigen-presenting cells expressing DC-SIGN (CD209) in the decidua of early human pregnancy*, Am J Pathol. 162(3):887-96 [2003]). These C-type lectins, therefore, qualify as major players in the horizontal and vertical transmission of HIV within a given individual (Geijtenbeek T B, van Kooyk Y, *DC-SIGN: a novel HIV receptor on DCs that mediates HIV-1 transmission*, Curr Top Microbiol Immunol 276:31-54 [2003]). In vivo, DC-SIGN is not only expressed by myeloid DCs, but also by subpopulations of macrophages, which are another main group of HIV reservoir cells (Soilleux E J et al., *Constitutive and induced expression of DC-SIGN on dendritic cell and macrophage subpopulations in situ and in vitro*, J Leukoc Biol. 71(3):445-57 [2002]).

It is known that DC-SIGN is an endocytic adhesion receptor.

First, DC-SIGN-attached particles are shuttled into the MHC class II antigen processing and presentation pathway and are accessed to the mechanism generating T-cell immunity (as desirable in case of any viral infection), as well as B-cell immunity (as supportive in the clearance of virus, by mechanisms secondary to the generation of antibodies, such as Fc receptor-mediated phagocytosis or, in case of cytotoxic antibodies, complement-mediated lysis) (e.g., Schjetne K W et al., *Mouse C specific T cell clone indicates that DC-SIGN is an efficient target for antibody-mediated delivery of T cell epitopes for MHC class II presentation*, lift Immunol 14(12): 1423-30 [2002]; Engering, A et al., *The dendritic cell-specific adhesion receptor DC-SIGN internalizes antigen for presentation to T cells*, J Immunol 168(5):2118-26 [2002]).

Second, Turville et al., demonstrated that Th-cell infection by MyDCs with HIV-1 is a two-phased process that depends on the DCs' developmental stage, including both directional transport of virus to the immunological synapse, as well as active de-novo synthesis of HIV-1 from proviral DNA (Turville S G, Santos J J, Frank I et al. *Immunodeficiency virus uptake, turnover, and two-phase transfer in human dendritic cells*, Blood; online publication ahead of print: DOI 10.1182/blood-2003-09-3129 [2003]). In addition, the important roles of DC-SIGN in the migratory transport of virus by MyDCs (Geijtenbeek T B H, van Kooyk Y, *DC-SIGN: a novel HIV receptor on DCs that mediates HIV-1 transmission*, Curr Top Microbiol Immunol; 276:31-54 [2003]) and in the in trans infection of Th cells (Geijtenbeek T B H, Kwon D S, Torensma R et al. *DC-SIGN a dendritic cell-specific HIV-1-binding protein that enhances trans-infection of T cells*, Cell; 100:587-97 [2000]) very much support a pathogenetic key role for these cells. Intriguingly, it has now been shown that passive transfer from MyDCs to Th cells via DC-SIGN requires that HIV-1 is first internalized into intracellular trypsin-resistant compartments (McDonald D, Wu L, Bohks S M, KewalRamani V N, Unutmaz D, Hope T J, *Recruitment of HIV and its* receptors to dendritic cell-T cell junctions, Science; 300: 1295-7[2003]; Kwon D S, Gregorio G, Bitton N, Hendrickson W A, Littman D R, *DC-SIGN-mediated internalization of HIV is required for trans-enhancement of T cell infection, Immunity;* 16:135-44 [2002]). Indeed, after infection with HIV-1, intracytoplasmic compartments with accumulated infectious virus are demonstrable in both immature and mature MyDCs (Frank I, Piatak M Jr, Stoessel H, Romani N, Bonnyay D, Lifson J D, Pope M, *Infectious and whole inactivated simian immunodeficiency viruses interact similarly with primate dendritic cells (DCs): differential intracellular fate of virions in mature and immature DCs,* J Virol; 76:2936-51 [2002]).

Highly Active Antiretroviral Therapy (HAART) has been shown to be effective to reduce the plasma viral load to undetectable levels in HIV-infected individuals and to markedly diminish the number of HIV-1 RNA copies in secondary lymphoid tissues (Wong, J. K. et al., *Recovery of replication-competent HIV despite prolonged suppression of plasma viremia,* Science, 278:1291-1295 [1997]; Cavert, W. et al., *Kinetics of response in lymphoid tissues to antiretroviral therapy of HIV-1 infection,* Science 276(5314):960-964 [1997]). However, the capacity of HIV-1 to establish latent infection allows viral particles to persist in tissues despite immune responses and antiretroviral therapy (Gangne J-F, Desormeaux A, Perron S, Tremblay M. J, Bergeron M. G, *Targeted delivery of indinavir to HIV-1 primary reservoirs with immunoliposomes,* Biochim Biophys Acta, 1558: 198-210 [2002]). It is hypothesized that the susceptibility of dendritic cells to being infected with HIV, together with their crucial immunologic function, leads to the continuous spread of HIV. Therefore, it has been suggested that targeting of anti-virals to these reservoir cells is an important goal to achieve permanent reconstitution of adaptive immunity (Gieseler R K, Marquitan G, Scolaro M J, Cohen M D, *Lessons from history: dysfunctional APCs, inherent dangers of STI and an important goal, as yet unmet,* Trends Immunol 24:11 [2003]).

Liposomes are a suitable vehicle for specifically delivering encapsulated compounds to any given cell type, provided the existence of an appropriate targeting structure. Because of its highly restricted cellular expression, DC-SIGN qualifies as such a targeting molecule. We have earlier shown inhibition of HIV propagation in infected peripheral blood mononuclear leukocytes after liposomal delivery of sense DNA directed towards the HIV 5' tat splice acceptor site (Sullivan S M, Gieseler R K, Lenzner S, Ruppert J, Gabrysiak T G, Peters J H, Cox G, Richer L, Martin W J, Scolaro M J, *Inhibition of human immunodeficiency virus-1 proliferation by liposome-encapsulated sense DNA to the 5' tat splice acceptor site,* Antisense Res Dev; 2:187-97 [1992]).

Since the discovery in the 1960s that hydration of dry lipid film forms enclosed spherical vesicles or liposomes that resemble miniature cellular organelles with lipid bilayers, the potential use of lipid-drug complexes as biodegradable or biocompatible drug carriers to enhance the potency and reduce the toxicity of therapeutics was recognized (e.g., Bangham A D, *Liposomes: the Babraham connection,* Chem Phys Lipids 64:275-285 [1993]). Lipid-drug complexes have long been seen as a potential way to improve the Therapeutic Index (TI) of drugs by increasing their localization to specific organs, tissues or cells. The TI is the ratio between the median toxic dose (TD50) and the median effective dose (ED50) of a particular drug. However, application of lipid-drug complexes to drug delivery systems was not realized until 30 years later. Only then were the first series of liposome-based therapeutics approved for human use by the U.S. Food and Drug Administration (FDA). Liposomes have been used as drug carriers in pharmaceutical applications since the mid-1990s (Lian, T. and Ho, R. J. Y., *Trends and Developments in Liposome Drug Delivery Systems,* J. Pharm. Sci. 90(6):667-80 [2001]).

Although the lipid constituent can vary, many formulations use synthetic products of natural phospholipid, mainly phosphatidylcholine. Most of the liposome formulations approved for human use contain phosphatidylcholine (neutral charge), with fatty acyl chains of varying lengths and degrees of saturation, as a major membrane building block. A fraction of cholesterol (~30 mol %) is often included in the lipid formulation to modulate rigidity and to reduce serum-induced instability caused by the binding of serum proteins to the liposome membrane.

Based on the head group composition of the lipid and the pH, liposomes can bear a negative, neutral, or positive charge on their surface. The nature and density of charge on the surface of the liposomes influences stability, kinetics, and extent of biodistribution, as well as interaction with and uptake of liposomes by target cells. Liposomes with a neutral surface charge have a lower tendency to be cleared by cells of the reticuloendothelial system (RES) after systemic administration and the highest tendency to aggregate. Although negatively charged liposomes reduce aggregation and have increased stability in suspension, their nonspecific cellular uptake is increased in vivo. Negatively charged liposomes containing phosphatidylserine (PS) or phosphatidylglycerol (PG) were observed to be endocytosed at a faster rate and to a greater extent than neutral liposomes (Allen T M, et al., *Liposomes containing synthetic lipid derivatives of poly(ethylene glycol) show prolonged circulation half-lives in vivo,* Biochim Biophys Acta 1066:29-36 [1991]; Lee R J, et al., *Folate-mediated tumor cell targeting of liposome-entrapped doxorubicin in vitro,* Biochim Biophys. Acta 1233:134-144). Negative surface charge is recognized by a variety of receptors on various cell types, including macrophages (Allen T M et al. [1991]; Lee R J, et al., *Delivery of liposomes into cultured KB cells via folate receptor-mediated endocytosis,* J Biol Chem 269:3198-3204 [1994]).

Inclusion of some glycolipids, such as the ganglioside $GM_1$ or phosphotidylinositol (PI), inhibits uptake by macrophages and RES cells and results in longer circulation times. It has been suggested that a small amount of negatively charged lipids stabilize neutral liposomes against an aggregation-dependent uptake mechanism (Drummond D C, et al., *Optimizing liposomes for delivery of chemotherapeutic agents to solid tumors,* Pharmacol Rev 51:691-743 [1999]). Positively charged (i.e. cationic) liposomes, often used as a DNA condensation reagent for intracellular DNA delivery in gene therapy, have a high tendency to interact with serum proteins; this interaction results in enhanced uptake by the RES and eventual clearance by lung, liver, or spleen. This mechanism of RES clearance partly explains the low in vivo transfection efficiency. Other factors, including DNA instability, immune-mediated clearance, inflammatory response, and tissue accessibility can also contribute to low transfection efficiency in animals. In fact, high doses of positively charged liposomes have been shown to produce varying degrees of tissue inflammation (Scheule R K, et al., *Basis of pulmonary toxicity associated with cationic lipid-mediated gene transfer to the mammalian lung,* Hum Gene Ther 8:689-707 [1997]).

The surface of the liposome membrane can be modified to reduce aggregation and avoid recognition by the RES using hydrophilic polymers. This strategy is often referred to as surface hydration or steric modification. Surface modification is often done by incorporating gangliosides, such as $GM_1$, or lipids that are chemically conjugated to hygroscopic or hydrophilic polymers, usually polyethyleneglycol (PEG). This technology is similar to protein PEGylation. Instead of conjugating PEG to therapeutic proteins such as adenosine deaminase (Alderase, for treatment of severe combined immunodeficiency syndrome) to reduce immune recognition and rapid clearance (Beauchamp C, et al., *Properties of a novel PEG derivative of calf adenosine deaminase*, Adv Exp Med Biol 165:47-52 [1984]), PEG is conjugated to the terminal amine of phosphatidylethanolamine. This added presence of hydrophilic polymers on the liposome membrane surface provides an additional surface hydration layer (Torchilin V P, *Immunoliposomes and PEGylated immunoliposornes: possible use of targeted delivery of imaging agents*, Immunomethods 4:244-258). The resulting liposomes can be recognized neither by macrophages nor the RES as foreign particles, and thus escape phagocytic clearance. A number of systematic studies have determined the optimum size of PEG polymer and the density of the respective polymeric PEG lipid in the liposome membrane.

Early research has demonstrated that the liposome size affects vesicle distribution and clearance after systemic administration. The rate of liposome uptake by RES increases with the size of the vesicles (Hwang K, *Liposome pharmacokinetics*, In: Ostro M J, editor, Liposomes: from biophysics to therapeutics, New York: Marcel Dekker, pp. 109-156 [1987]). Whereas RES uptake in vivo can be saturated at high doses of liposomes or by predosing with large quantities of control liposomes, this strategy may not be practical for human use because of the adverse effects related to sustained impairment of physiological functions of the RES. The general trend for liposomes of similar composition is that an increasing size results in enhanced uptake by the RES (Senior J, et al., *Tissue distribution of liposomes exhibiting long half-lives in the circulation after intravenous injection*, Biochim Biophys Acta 839:1-8 [1985]). Most recent investigations have used unilamellar vesicles, 50-100 nm in size, for systemic drug delivery applications. For example, the antifungal liposome product AmBisome is formulated to the size specification of 45-80 nm to reduce RES uptake. Serum protein binding is an important factor that affects liposome size and increases the rate of clearance in vivo. Complement activation by liposomes and opsonization depend on the size of the liposomes (Devine D V, et al., *Liposome-complement interactions in rat serum: Implications for liposome survival studies*, Biochim Biophys Acta 1191:43-51 [1994]; Liu D, et al., *Recognition and clearance of liposomes containing phosphatidylserine are mediated by serum opsonin*, Biochim Biophys Acta 1235:140-146 [1995]). Even with the inclusion of PEG in the liposome compositions to reduce serum protein binding to liposomes, the upper size limit of long-circulation PEG-PE liposomes is ~200 nm. Due to biological constraints, development of long circulating large (>500 nm) liposomes using steric stabilization methods has not been successful. Hence, considerations of liposome size and its control in manufacturing at an early stage of drug development provide a means to optimize efficiency of liposome drug delivery systems.

The exact mechanisms of biodistribution and disposition in vivo vary depending on the lipid composition, size, charge, and degree of surface hydration/steric hindrance. In addition, the route of administration may also influence the in vivo disposition of liposomes. Immediately after intravenous administration, liposomes are usually coated with serum proteins and taken up by cells of the RES and eventually eliminated. (Chonn A, et al., *Association of blood proteins with large unilamellar liposomes in vivo. Relation to circulation lifetimes*, J Biol Chem 267:18759-18765 [1992]; Rao M, et al., *Delivery of lipids and liposomal proteins to the cytoplasm and Golgi of antigen presenting cells*, Adv Drug Deify Rev 41:171-188 [2000]). Plasma proteins that can interact with liposomes include albumin, lipoproteins (i.e., high-density lipoprotein [HDL], low-density lipoprotein [LDL], etc.) and cell-associated proteins. Some of these proteins (e.g., HDL) can remove phospholipids from the liposome bilayer, thereby destabilizing the liposomes. This process may potentially lead to a premature leakage or dissociation of drugs from liposomes.

One of the key properties that make liposomes an invaluable drug delivery system is their ability to modulate the pharmacokinetics of liposome-associated and encapsulated drugs (Hwang K J, Padki M M, Chow D D, Essien H E, Lai J Y, Beaumier P L, *Uptake of small liposomes by non-reticuloendothelial tissues*, Biochim Biophys Acta; 901(1): 88-96 [1987]; Allen T M, Hansen C, Martin F, Redemann C, Yau-Young A, *Liposomes containing synthetic lipid derivatives of polyethylene glycol) show prolonged circulation half-lives in vivo*, Biochim Biophys Acta; 1066(1):29-36 [1991]; Allen T M, Austin G A, Chonn A, Lin L, Lee K C, *Uptake of liposomes by cultured mouse bone marrow macrophages: influence of liposome composition and size*, Biochim Biophys Acta; 1061(1):56-64 [1991]; Hwang, K. [1987]; Allen T, et al., *Pharmacokinetics of long-circulating liposomes*, Adv Drug Del Rev 16:267-284 [1995]). Relative to the same drugs in aqueous solution, significant changes in absorption, biodistribution, and clearance of liposome-associated drug are apparent, resulting in dramatic effects on both the efficacy and toxicity of the entrapped compound (Gabizon A, *Liposome circulation time and tumor targeting: implications for cancer chemotherapy*, Adv Drug Del Rev 16:285-294 [1995]; Bethune C, et al., *Lipid association increases the potency against primary medulloblastoma cells and systemic exposure of 1-(2-chloroethyl)-3-cyclohexyl-1-nitrosourea (CCNU) in rats*, Pharm Res 16:896-903 [1999]). However, therapeutic applications of systemically administered liposomes have been limited by their rapid clearance from the bloodstream and their uptake by the RES (Alving C, et al., *Complement-dependent phagocytosis of liposomes: suppression by 'stealth' lipids*, J Liposome Res 2:383-395 [1992]).

As already mentioned, circulation time can be increased by reducing the liposomesize and modifying the surface/steric effect with PEG derivatives. Also, liposomes with membranes engineered for sufficient stability escaping clearance by the RES are now available. Therefore, long-circulation liposomes that also significantly reduce toxicological profiles of the respective drugs can be used to maintain and extend plasma drug levels. Even though only a small fraction of liposomes eventually accumulate at target sites, prolonged circulation can indirectly enhance accumulation of liposome-associated drugs to targeted tissues.

It is a desideratum to actively enhance targeting of liposomes so as to direct them to the cell populations of interest before substantial clearance by the RES occurs. For example, immunoliposomes have been employed to target the erythrocyte reservoirs of intracellular malarial parasites (Owais, M. et al., *Chloroquine encapsulated in malaria-infected erythrocyte-specific antibody-bearing liposomes effectively controls chloroquine-resistant Plasmodium berghei infections in mice*, Antimicrob Agents Chemother 39(1):

180-4 [1995]; Singh, A M et al., *Use of specific polyclonal antibodies for site specific drug targeting to malaria infected erythrocytes in vivo*, Indian J Biochem Biophys 30(6):411-3 [1993]).

It is also a desideratum to apply lipid-drug delivery systems to the fight against the HIV/AIDS pandemic. More than 42 million people are estimated to be currently living with HIV/AIDS (UNAIDS [2002; 2003]). This global figure has been projected to increase considerably if no improved means of keeping this infection at bay will be developed and introduced to the global community (Morens D M, Folkers G K, Fauci A S, *The challenge of emerging and re-emerging infectious diseases*, Nature; 430:242-9 [2004]).

Anti-HIV drugs, such as nucleoside analogs (e.g., dideoxynucleoside derivatives, including 3'-azido-3'-deoxythymidine [AZT], ddC, and ddI), protease inhibitors, or phosphonoacids (e.g., phosphonoformic and phosphonoacetic acids), have previously been lipid-derivatized or incorporated into liposomes (e.g., Hostetler, K Y et al., Methods of treating viral infections using antiviral lipo-nucleotides, Ser. No. 09/846,398, US 2001/0033862; U.S. Pat. No. 5,223,263; Hostetler, K Y et al., *Lipid derivatives of phosphonoacids for liposornal incorporation and method of use*, U.S. Pat. No. 5,194,654; Gagne I F et al., *Targeted delivery of indinavir to HIV-1 primary reservoirs with immunoliposomes*, Biochim Biophys Acta 1558(2):198-210 [Feb. 2002]). Still, in one report, subcutaneous injection of liposome-encapsulated ddI to C57BL/6 mice, resulted in low accumulation of liposomes in lymph nodes, compared to intravenous injection (Harvie, P et al., *Lymphoid tissues targeting of liposome-encapsulated 2',3'-dideoxylnosine*, AIDS 9(7):701-7 [1995]).

The use of specific vector molecules coupled to, or embedded within, a liposome surface, has been described for enhanced transmembrane delivery and uptake of liposome-encapsulated compounds that otherwise are only insufficiently delivered into a cell, or that are not efficiently delivered to a specifically desirable intracellular organelle (reviewed in: Torchilin V P, Lukyanov A N, *Peptide and protein drug delivery to and into tumors: challenges and solutions*, Drug Discov Today 2003 Mar. 15; 8(6):259-66; Sehgal A, *Delivering peptides and proteins to tumors*, Drug Discov. Today 8(14):619 [2003]; Koning G A, Storm G, *Targeted drug delivery systems for the intracellular delivery of macromolecular drugs*, Drug Discov Today 2003 Jun. 1; 8(11):482-3). Such vectors molecules include so-called protein transduction domains (PTDs), which are derived from various viruses or from *Drosophila antennapedia*. Of special interest for application in HIV disease are HIV Tat and its derivatives which act as PTDs (e.g., Schwarze, S. R., et al., *In vivo protein transduction: delivery of a biologically active protein into the mouse*, Science 285:1569-72 [1999]).

Anti-HIV drugs have been encapsulated in the aqueous core of immunoliposomes, which include on their external surfaces antigen-specific targeting ligands (e.g., Bergeron, M G. et al., *Targeting of infectious agents bearing host cell proteins*, WO 00/66173 A3; Bergeron, M G. et al., *Liposomes encapsulating antiviral drugs*, U.S. Pat. No. 5,773,027; Bergeron, M G. et al., *Liposome formulations for treatment of viral diseases*, WO 96/10399 A1; Gagne J F et al., *Targeted delivery of indinavir to HIV-1 primary reservoirs with immunoliposomes*, Biochim Biophys Acta 1558 (2):198-210 [2002]; Dufresne I et al., *Targeting lymph nodes with liposomes bearing anti-HLA-DR Fab' fragments*, Biochim Biophys Acta 1421(2):284-94 [1999]; Bestman-Smith J et al., *Sterically stabilized liposomes bearing anti-HLA-DR antibodies for targeting the primary cellular reservoirs of HIV-1* Biochim Biophys Acta 1468(1-2):161-74 [2000]; Bestman-Smith J et al., *Targeting cell-free HIV and virally-infected cells with anti-HLA-DR immunoliposomes containing amphotericin B*, AIDS 10; 14(16):2457-65 [2000]).

There are many examples of antibody-targeted liposomes in animal models. Currently, there is also at least one antibody-targeted liposome, termed DOXIL, evaluated clinically. By employing a single-chain antibody that had been raised against ITER2/neu, it is targeted to certain types of breast cancer. Developed by Papahadjopoulos and colleagues at UCSF, this antibody-mediated targeting variant is currently being evaluated in clinical trials at the National Cancer Institute (e.g., Park J W, Hong K, Kirpotin D B, Colbem G, Shalaby R, Baselga J, Shao Y, Nielsen U B, Marks J D, Moore D, Papahadjopoulos D, Benz C C, *Anti-HER2 Immunoliposomes: enhanced efficacy attributable to targeted delivery*, Clin Cancer Res. 2002 April; 8(4):1172-81 [2002]).

Attempts at active targeting of lymphoid cell populations with liposomes have met with some degree of success. Bestman-Smith et al. (2000) reported that after subcutaneous injection of immunoliposomes bearing anti-HLA-DR Fab' fragments into mice, there was accumulation of the immunoliposomes in lymphoid tissues (Bestman-Smith J et al., *Targeting cell-free HIV and virally-infected cells with anti-HLA-DR immunoliposomes containing amphotericin B*, AIDS 10; 14(16):2457-65 [2000]). Gagne J F et al. [2002] reported that subcutaneous injections of immunoliposome-encapsulated anti-HIV drugs resulted in an accumulation of the drug in lymph nodes of injected mice with relatively low toxicity, compared to administration of the free drug; there was no significant difference reported in the ability of anti-HLA-DR-targeted immunoliposomes containing indinavir to inhibit HIV-1 replication in infected PMI cells, compared to free indinavir or non-targeted liposomal-indinavir complexes. Copland et al. targeted the mannose receptors of monocyte-derived dendritic cells (Mo-DCs) and reported that mannosylated liposomes were preferentially bound and taken up by Mo-DCs at 37° C., compared to non-mannosylated neutral liposomes and negatively charged liposomes (Copland, M J et al., *Liposomal delivery of antigen to human dendritic cells*, Vaccine 21:883-90 [2003]).

The present invention provides a liposomal delivery system that facilitates the targeting of active agents, such as drugs, immunomodulators, lectins or other plant-derived substances specifically to myeloid cell populations of interest. The present invention therefore addresses, inter alia, the need to target the reservoirs of HIV, hepatitis C virus (HCV) in myeloid cells, particularly dendritic cells and macrophages, as well as follicular dendritic cells of myeloid origin, of persons infected with HIV and those suffering from AIDS, or persons infected or co-infected with HCV and those suffering from HCV-dependent pathologic alterations of the liver. In addition, the present invention may allow for indirect targeting of lymphoid cells, particularly T cells, upon their physical interaction with myeloid cells. Moreover, the present invention may allow for the specific elimination, or down-modulation, of malignant tumor cells or immune cells mediating autoimmunity; the enhancement of DC-dependent autologous tumor immunization; the therapeutic down-regulation of autoimmune diseases; or the DC-tropic stimulation of specific adaptive immunity (both in terms of vaccination or treatment) against common pathogens, or pathogens potentially employed as agents of bioterrorism, for which there currently exists no efficient protection. The present invention may also allow for biotechnological advancement, such as, inter alia, by targeting DCs for increasing the production of monoclonal antibodies, or by allowing for the production of such immunoglobulins that cannot be induced in the absence of inductive liposomal DC targeting.

SUMMARY OF THE INVENTION

The present invention relates to a method of preferentially, or "actively," targeting and delivering an active agent, such as a drug, to a mammalian immune cell, in vivo or in vitro.

In particular, the present invention is directed to a method of preferentially targeting a liposome to a mammalian immune cell, such as a myeloid progenitor cell, a monocyte, a dendritic cell, a macrophage or a T-lymphocyte. The method involves administering to the immune cell, in vitro or in vivo, a liposome comprising an active agent and further comprising an outer surface that comprises at least one targeting ligand that specifically binds a marker on the surface of the immune cell, such as CD209 (DC-SIGN), CD45RO, CD4, or HLA class II.

The present invention is also particularly directed to a method of preferentially delivering a drug to an immune cell of a mammalian subject, including a human. The targeted immune cells include myeloid progenitor cells, monocytes, dendritic cells, macrophages or T-lymphocytes. The method involves injecting into the mammalian subject a lipid-drug complex, for example, but not limited to a liposome that comprises the drug and further comprises an outer surface comprising at least one targeting ligand that specifically binds a marker on the surface of the immune cell, such as, but not limited, to CD209 (DC-SIGN), the immune cell being infected with, or susceptible to infection with, an infectious agent, such as, but not limited to, human immunodeficiency virus, types 1 and 2 (HIV-1; HIV-2).

The present invention is also directed to inventive targeted liposomes. One embodiment of the targeted liposome comprises on its external surface a targeting ligand that specifically binds CD209. Another embodiment of the targeted liposome comprises on its external surface a targeting ligand that specifically binds CD209 and a targeting ligand that specifically binds CD4. The inventive targeted liposomes are useful for targeting immune cells, such as dendritic cells.

The presence of HIV-1 in reservoir cells, e.g. dendritic cells, leads to the continuous de-novo infection of naïve T cells within the lymphoid organs and tissues of an infected person. It has been hypothesized that eradication of such sanctuary sites may eventually eliminate HIV-1 from the individual. The present invention provides a targeting system which, via targeting ligands such as the dendritic cell-specific molecule DC-SIGN, delivers chemical compounds directly into these cells. Thus, the present invention is particularly, but not exclusively, of benefit for delivering antiviral drugs, packaged in immunoliposomes, to myeloid- and lymphoid-derived immune cells harboring HIV-1 or HIV-2, such as the HIV reservoir in dendritic cells. Another benefit of the present invention, by actively targeting immune cells, is in providing vaccination strategies against HIV (e.g., Steinman R M, Granelli-Piperno A, Pope M, Trumpfheller C, Ignatius R, Anode G, Racz P, Tenner-Racz K, *The interaction of immunodeficiency viruses with dendritic cells*, Curr Top Microbiol Immunol 276:1-30 [2003]; Pope M, *Dendritic cells as a conduit to improve HIV vaccines*, Curr Mol Med 3:229-42 [2003]). Additional benefits provided by the present invention include utility in the treatment of conditions involving abnormal proliferation of immune cells, e.g., primary and metastatic lymphoid cancers (lymphomas and leukemias), solid tumors or their post-surgical remnants, or autoinurnune diseases, including specifically targeting immune cells in gene therapy applications. The present invention also provides a way to target dendritic cells for facilitating the production of anti-infective vaccines, anti-bioterrorism vaccines, anti-cancer vaccines, or biotechnological and therapeutic tools such as monoclonal antibodies.

The present invention is also directed to variations on the inventive targeted delivery system. Any type of cell residing within any kind of organ system (such as the endocrine or the nervous systems), as well as any type of anatomic entity (such as the urogenital or the respiratory tracts) can be targeted selectively by the respective liposomal variant containing its respective targeting ligand on the external surface and its active agent of choice.

BRIEF DESCRIPTION OF THE FIGURES

FIGS. 3A, 3B, and 3C illustrate liposomal targeting of DCs via two cell markers (termed bispecific targeting), including time dependency of the targeting efficacy over a 24-h period. Mature MoDCs were generated according to protocol described herein and investigated for uptake of different constructs of targeted Protein A liposomes bearing 2-member combinations of anti-CD4, anti-CD45R0 and anti-CD209 mAbs. The MoDCs were co-incubated with the liposomes for 1, 3 or 24 h and then harvested and tested by flow cytometry. Control mAbs were used to detect cellular surface expression of the respective antigens (column headed "Marker Expression"). Empty curves indicate isotype controls; shaded curves indicate test conditions. FIG. 3A shows results for the combination of anti-CD4 plus anti-CD45R0 targeting ligands. FIG. 3B shows results for the combination of anti-CD4 plus anti-CD209 targeting ligands. FIG. 3C shows results for the combination of anti-CD45R0 plus anti-CD209 targeting ligands.

FIG. 4A shows arithmetic means and upper extremes of n=2 independent experiments; FIG. 4B factors derived from arithmetic means), and MoDCs targeted with corresponding immunoliposomes (calcein fluorescence).

DETAILED DESCRIPTION OF THE PREFERRED EMBODIMENTS

Figure 1:
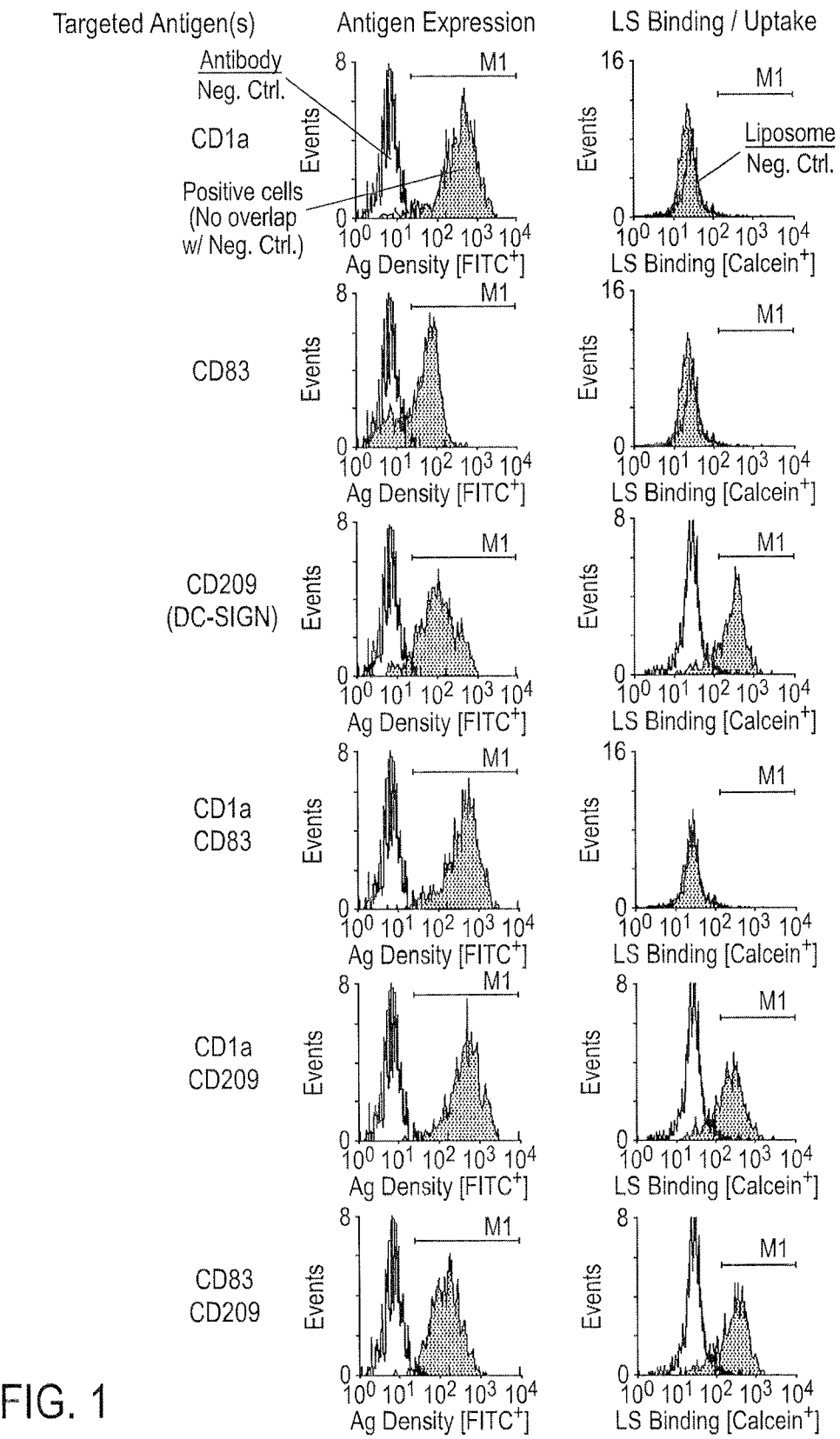
FIG. 1 shows time-dependent targeting of calcein-labeled liposomes to Mo-DCs mediated by DC-SIGN or other targeting ligands, including bispecific combinations. The column entitled "Antigen Expression" shows phenotypic expression of the respective marker(s), as tested with the mAbs only. Detection was by flow cytometry with a mAb-conjugated fluorescent dye, fluorescein-5-iothiocyanate (FITC); the column "LS Binding/Uptake" shows successful targeting and uptake, as evidenced by intracellular delivery of a liposome-encapsulated fluorescent dye, calcein.

The present invention relates to a method of preferentially delivering an active agent, such as a drug, to a mammalian immune cell. In some embodiments, delivery is in vitro, and in other embodiments delivery of the active agent is in vivo.

The term "preferentially" refers to the fact that the lipid-drug complex, or the liposome, is delivered to the cell and the active agent (e.g., the drug) is taken up by the cell, more effectively than delivery and uptake of the agent using a comparable lipid-drug complex, or liposome, having an outer surface that does not comprise the at least one targeting ligand, in contrast with the invention.

The targeted immune cells include myeloid progenitor cells, monocytes, dendritic cells (DCs), macrophages, and T-lymphocytes.

Monocytes are one of the types of cells produced by the myeloid differentiation lineage of the bone marrow. It has been shown that DCs can likewise be derived from monocytes or other types of cells, i.e. mainly progenitor cells, generated within the myeloid lineage (e.g., Peters J H, Ruhl S, Friedrichs D, *Veiled accessory cells deduced from monocytes*, Immunobiology 176(1-2):154-66 [1987]; Gieseler R, Heise D, Soruri A, Schwartz P, Peters J H, In-vitro differentiation of mature dendritic cells from human blood monocytes, Dev. Immunol. 6(1-2):25-39 [1998]; Gieseler R K H, Rüber R-A, Kuhn R, Weber K, Osborn M, Peters J H, *Dendritic accessory cells derived from rat bone marrow precursors under chemically defined conditions in vitro belong to the myeloid lineage*, Eur J Cell Biol 54(1):171-81 [1991]). As a consequence, monocyte-derived dendritic cells (MoDCs) are a subset of MyDCs.

A dendritic cell includes a "myeloid dendritic cell" (My-DC), i.e., a "myeloid lineage-derived DC", which includes a monocyte-derived dendritic cell (Mo-DCs) as well as other DC types such as, for example, promonocyte-derived dendritic cells. (e.g., Steinbach F, Gieseler R, Soruri A, Krause B, Peters J H, *Myeloid DCs deduced from monocytes, In-vitro and in-vivo data support a monocytic origin of DCs*, Adv Exp Med Biol. 1997; 417:27-32 [1997]). A dendritic cell also includes a "lymphoid dendritic cell" (Ly-DC), i.e., a "lymphoid lineage-derived DC"; the only type of DC presently known to derive from the lymphoid lineage is the plasmacytoid dendritic cell (pc-DC) (Facchetti F, Vermi W, Mason D, Colorma M, *The plasmacytoid monocyte/interferon producing cells*, Virchows Arch; 443(6):703-17. Epub 2003 Oct. 28 [2003]). A dendritic cell also includes a follicular dendritic cell (FDC). It currently is still controversial whether FDCs derive from the myeloid, the lymphoid or a separate lineage; (Haberman A M, Shlomchik M J, *Reassessing the function of immune-complex retention by follicular dendritic cells*, Nat Rev Immunol; 3(9):757-64 [2003]). For an overview of all types of dendritic cells, confer to Donaghy H, Stebbing J, Patterson S, *Antigen presentation and the role of dendritic cells in HIV*, Curr Opin Infect Dis; 17(1):1-6 [2004].

A macrophage denotes a cell class comprising various organ-resident subtypes further including macrophages more typical of lymphoid or of non-lymphoid organs and tissues (e.g., Barreda D R, Hanington P C, Belosevic M, *Regulation of myeloid development and function by colony stimulating factors*, Dev Comp Immunol 3; 28(5):509-54 [2004]).

A T-lymphocyte includes, but is not limited to, a T-helper cell or a T-memory cell (Woodland D L, Dutton R W, *Heterogeneity of $CD4^+$ and $CD8^+$ T cells*, Curr Opin Immunol; 15(3):336-42 [2003]).

In accordance with some in-vivo embodiments of the invention a lipid-drug complex is injected into the mammalian subject, in which the immune cell is present.

In some embodiments, the immune cell is infected with, or susceptible to infection with, an infectious agent, such as a virus, a bacterium, a fungus, a protozoan, or a prion Examples of viral infectious agents are HIV-1 and HIV-2 (including all their clades), HSV, EBV, CMV, Ebola and Marburg virus, HAV, HBV, HCV and HPV.

In some embodiments, the immune cell is, in the presence or absence of infection, associated with the occurrence of an organ-specific or a systemic autoimmune disease. Examples of such diseases entities are Graves' disease; thyroid-associated ophthalmopathy (a.k.a. Graves' ophthalmopathy; a.k.a. endocrine ophthalmopathy); and multiple sclerosis (a.k.a. MS).

A "complex" is a mixture or adduct resulting from chemical binding or bonding between and/or among its constituents or components, including the lipid, drug, and other optional components of the inventive lipid-drug complex. Chemical binding or bonding can have the nature of a covalent bond, ionic bond, hydrogen bond, van der Waal's bond, hydrophobic bond, or any combination of these bonding types linking the constituents of the complex at any of their parts or moieties, of which a constituent can have one or a multiplicity of moieties of various sorts. Not every constituent of a complex needs to be bound to every other constituent, but each constituent has at least one chemical bond with at least one other constituent of the complex. In accordance with the present invention, examples of lipid-drug complexes include liposomes (lipid vesicles), or lipid-drug sheet disk complexes. Lipid-conjugated drugs can also be a part of the lipid-drug complex in accordance with the invention. However, drugs can also be associated with a lipid or a lipid complex in the absence of any type of chemical binding or bonding, such as is provided in the case of liposomes encapsulating a soluble drug in their aqueous interior space.

The lipid thug complex, e.g., the liposome, comprises an active agent, such as a drug. For purposes of the present invention, the drug is any drug known to be active against cellular proliferation or active against an infectious agent of interest.

The active agent, or drug, can be an anti-viral drug or virostatic agent, such as, interferon, a nucleoside analog, or a non-nucleoside anti-viral drug. Examples include anti-HIV drugs (e.g., a HIV reverse protease inhibitor), such as indinavir (a.k.a. Crixivan®, Merck & Co., Inc., Rahway, N.J.; saquinavir (N-tert-butyl-decahydro-2-[2(R)-hydroxy-4-phenyl-3(S)-[[N-(2-quinolylcarbonyl)-L-asparaginyl] amino] butyl]-(4aS,8aS)-isoquinoline-3(S)-carboxaraide; MW=670.86; a.k.a. Fortovase®, Roche Laboratories, Inc., Nutley, N.J.); or nelfinavir (i.e., nelfnavir mesylate, a.k.a. Viracept®; [3S-[2(2S*,3S*), 3a,4ab,8ab]]-N-(1,1-dimethylethyl)decahydro-2-[2-hydroxy-3[(3-hydroxy-2-methylbenzoyDamino]-4-(phenylthio)butyl]-3-isoquinolinecarboxamide mono-methanesulfonate (salt), MW=663.90 [567.79 as the free base]; Agouron Pharmaceuticals, Inc., La Jolla, Calif.). Other examples of antiviral drug include reverse transcriptase inhibitors, such as tenofovir disoproxil fumarate (9-[(R)-2-[[bis[[isopropoxycarbonyl)oxy]methoxy] phosphinyl] methoxy] propyl] adenine fumarate (1:1); MW=635.52; a.k.a. Viread®, Gilead Sciences, Foster City, Calif.). The anti-HIV drug can also be HIV-specific small interfering RNA (siRNA), anti-sense or sense DNA or RNA molecules.

In other embodiments, the active agent is an anticancer drug, an antifungal drug, or an antibacterial drug. In other embodiments, the active agent is an immunomodulatory agent (i.e., an immunoactivator, an immunogen, an immunosuppressant, or an anti-inflammatory agent), such as cyclosporin, steroids and steroid derivatives. Other examples of useful drugs, in accordance with the invention, include therapeutic cytotoxic agents (e.g., cisplatin, carboplatin, methotrexate, 5-fluorouracil, and amphotericin), naked DNA expression vectors, therapeutic proteins, therapeutic oligonucleotides or nucleotide analogs, interferon, cytokines, or cytokine agonists or antagonists. Also useful as a drug is a cytotoxic alkylating agent, such as, but not limited to, busulfan (1,4-butanediol dimethanesulphonate; Myleran, Glaxo Wellcome), clalorambucil, cyclophosphamide, melphalan, or ethyl ethanesulfonic acid. Such drugs or agents are particularly useful in treating conditions involving pathological proliferation of immune cells, for example, lymphoid cancers or autoimmune diseases.

In other embodiments, the active agent is a natural substance with therapeutic properties or benefits, such as plant-derived substances in purified or recombinant form. Examples of plant-derived substances include leaf extract IDS 30, rhizome derived UDA lectin, and MHL.

The present invention contemplates the selective employment of natural substances that have been long acknowledged for their therapeutic properties and potentials in many cultures worldwide. One of such plant-derived substances, salicylic acid, which is found at varying concentrations in the bark of many trees, has served as the starter substance for one of nowadays great remedies, acetyl salicylic acid (ASS), or Aspirin, respectively. As to the present invention, the stinging nettle (*Urtica dioica*) is a prominent example from the numerous plants that have been known for centuries to have great therapeutic benefits. Recent scientific investigation concerning the action of some of the components of *Urtica dioica* provides an opportunity for their targeted application.

For example, MyDCs play an important role in the initiation of rheumatoid arthritis (RA) which is an example for a disease crossing the border between autoimmune and inflammatory conditions. Broer and Behnke have shown that the *Urtica dioica* leaf extract IDS 30 (Hox-α), which has been recommended for adjuvant therapy of RA, prevents the phenotypic/functional maturation of MyDCs; diminishes the secretion of tumor necrosis factor-α; and reduces the T cell-stimulating capacity of MyDCs, while it dose-dependently increases the expression of chemokine receptor 5 and CD36 as well as the endocytic capacity of these cells. The authors suggested that these effects of IDS 30 may contribute to its therapeutic effect on T cell-mediated autoimmune/inflammatory diseases such as RA (Broer J, Behnke B, *Immunosuppressant effect of IDS* 30, *a stinging nettle leaf extract, on myeloid dendritic cells in vitro*, J Rheumatol; 29(4):659-66 [2002]). It is reasonable to assume that inhibition of the transcription factor NF-κB is involved in this process (Riehemann K, Behnke B, Schulze-Osthoff K, Plant extracts from stinging nettle (*Urtica dioica*), an antirheumatic remedy, inhibit the proinflammatory transcription factor NF-κB, FEBS Lett; 442(1):89-94 [1999]), so that this extract or its active purified ingredients may inhibit a great number of debilitating or life-threatening pathogenic conditions that depend on the hyperactivation of NF-κB.

Lectins are another example of a natural substance that has therapeutic properties and potentials. Lectins (i.e., carbohydrate-binding proteins with agglutinating properties) are produced by a number of plants, mainly in their roots or rhizomes, as vital components of their own immune systems. Shibuya et al. first described the sugar-binding properties of the stinging nettle lectin (Shibuya N, Goldstein U, Shafer J A, Peumans W J, Broekaert W F, (Carbohydrate binding properties of the stinging nettle (*Urtica dioica*) rhizome lectin, Arch Biochem Biophys; 249(1):215-24 [1986]). The (GlcNAc)n-specific lectin from the stinging nettle, termed *Urtica dioica* agglutinin (UDA), has been shown to inhibit HIV-1-, HIV-2-, CMV-, RSV-, and influenza A virus-induced cytopathicity at an EC50 ranging from 0.3 to 9 μg/ml as well as syncytium formation between persistently HIV-1- and HIV-2-infected HUT-78 cells and CD4+ Molt/4 (clone 8) cells (EC50: 0.2-2 μg/ml). It has been suggested that UDA may act as a virion/target cell fusion inhibitor (Balzarini J, Neyts J, Schols D, Hosoya M, Van Damme B, Peumans W, De Clercq E. The mannose-specific plant lectins from Cymbidium hybrid and Epipactis helleborin and the (N-acetylglucosamine)n-specific plant lectin from *Urtica dioica* are potent and selective inhibitors of human immunodeficiency virus and cytomegalovirus replication in vitro. Antiviral Res18(2):191-207 [1992]). Such an action, if verified, may relate to UDA's superantigen nature (Galelli A, Truffa-Bachi P, *Urtica dioica* agglutinin. A superantigenic lectin from stinging nettle rhizome, J Immuno 1; 151(4): 1821-31 [1993]).

Again, the rhizome-derived UDA lectin, in addition to the leaf-derived IDS-30 extract, act therapeutically on certain autoimmune diseases. This superantigen has been shown to induce a rapid deletion of a large fraction of T-cell receptor Vβ38.3-expressing mature T-cells (Delcourt M, Peumans W J, Wagner M C, Truffa-Bachi P, Vβ-specific deletion of mature thymocytes induced by the plant superantigen *Urtica dioica* agglutinin, Cell Immunol; 168 (2): 158-64 [1996]). In mice, this activity has been demonstrated to prevent the development of systemic lupus erythematosus, as UDA-treated animals did not develop overt clinical signs of lupus and nephritis (Musette P, Galelli A, Chabre H, Canard P, Peumans W, Truffa-Bachi P, Kourilsky P, Gachelin G, *Urtica dioica* agglutinin, a V(38.3-specific superantigen, prevents the development of the systemic lupus erythematosus-like pathology of MRL 1pr/lpr mice, Eur J Immunol; 26(8): 1707-11 [1996]).

These are just two of several examples of *Urtica dioica*-derived substances, as well as the constituents of many other plants, that act therapeutically, either as single molecules, or their oligomers, or in combination, on defined immune cells (such as MyDCs). Pathologic conditions with which these substances interfere include infectious, neoplastic, and autoimmune diseases. The liposomal system described herein may be utilized to specifically encapsulate such molecular plant components in purified or recombinant form, and address cells that have been, or will be, identified as their specific targets, so as to dramatically increase their effect and harness their potential while considerably reducing the risk of toxic side effects.

In addition, liposomes shuttled into intracellular compartments, such as endosomes, may deliver lectins suitable to agglutinate intracellularly stored pathogens (including HIV-1, HCV, the Ebola virus, Mycobacterium tuberculosis, and others), so as to generate large lectin-pathogen complexes that may, thus be recognized by the infected cell and, subsequently, be degraded enzymatically and/or pH-dependently. For example, one lectin that is highly suitable for this purpose when addressing the HIV-1 reservoirs is the *Myrianthus holstii* lectin (MILL, a.k.a. Myrianthin) which is obtained from the roots of the Tanzanian plant *Myrianthus holstii*. MHL comprises several favorable characteristics, namely agglutination of HIV-1; no toxicity for greater than two orders of magnitude above the effective dosage in 50% of infected cells ($EC_{50}$); and the lack of mitogenicity for human leukocytes (Charan R D, Munro M H, O'Keefe B R, Sowder R C I I, McKee T C, Currens M J, Pannell L K, Boyd M R, Isolation and characterization of *Myrianthus holstii* lectin, a potent HIV-1 inhibitory protein from the plant *Myrianthus holstii*, J Nat Prod 2000 August; 63(8): 1170-4).

Compounds such as UDA, MIL and many others lectins or agglutinins, respectively, may be encapsulated within liposomes, so as to selectively unfold their properties within a given targeted cell and, more specifically, inside a specified intracellular compartment(s) of such a cell, or cell types.

Some embodiments of the inventive method of preferentially targeting a mammalian immune cell with a liposome relate to improved means of vaccination. In this case, active targeting of dendritic cells, in accordance with the invention, is used for vaccinating against cancer, or against a virus such as HIV. (E.g., Nair, S et al., *Soluble proteins delivered to dendritic cells via pH-sensitive liposomes induce primary cytotoxic T lymphocyte responses in vitro*, J. Exp. Med. 175(2):609-12 [1992]; Philip, R et al., *Transgene expression in dendritic cells to induce antigen-specific cytotoxic T cells in healthy donors*, Cancer Gene Ther. 5(4):236-46 [1998]; Ludewig, B et al., *Protective antiviral cytotoxic T cell memory is most efficiently maintained by restimulation via dendritic cells*, J. Immunol. 163(4):1839-44 [1999]; Chikh, G and Schutze-Redelmeier, M P, *Liposornal delivery of CTL epitopes to dendritic cells*, Biosci. Rep. 22(2):339-53 [2002]; Grünebach, F et al. *Delivery of tumor-derived RNA for the induction of cytotoxic T-lymphocytes*, Gene Ther. 10(5):367-74 [2003]).

Targeting of dendritic cells in accordance with the invention is also useful for improving vaccination strategies in general via accessing intracellular endosomal MEC class I and/or MHC class II antigen processing compartments. (E.g. 7hou F and Huang L, *Liposome-mediated cytoplasmic delivery of proteins: an effective means of accessing the MHC class I-restricted antigen presentation pathway*, Immunomethods 1994; 4(3):229-35 [1994]; Owais M et al., Use of liposomes as an immunopotentiating delivery system: in perspective of vaccine development, Scand. J. Immunol. 54(1-2):125-32 [2001]; Mandal M and Lee I C D, *Listeriolysin O-liposome-mediated cytosolic delivery of macromolecule antigen in vivo: enhancement of antigen-specific cytotoxic T lymphocyte frequency, activity, and tumor protection*, Biochim. Biophys. Acta 1563(1-2):7-17). [2002]).

The inventive method of preferentially targeting a mammalian immune cell with a liposome can also be used to target dendritic cells for facilitating the production of monoclonal antibodies. (See, e.g., Berry J D et al., Rapid monoclonal antibody generation via dendritic cell targeting in vivo, Hybrid. Hybridomics 22(1):23-31 [2003]).

More than one drug can be incorporated by the lipid-drug complex, or liposome, in accordance with the inventive method, such that the lipid-drug complexes, e.g., liposomes, can incorporate a first drug and a second drug, or more drugs, in combination, as suits the particular needs of the practitioner. For example, useful liposomes can comprise a combination of an anti-HIV drug and an antifungal and/or antibacterial drug.

The present invention does not depend on any particular chemical or biochemical mechanism by which the useful formulations of lipid-drug complex, or liposome, are obtained or by which the drug is released to target cells.

Useful techniques for making lipid-drug complexes, such as liposomes, are known to the art (e.g., Sullivan S M, Gieseler R K H, Lenzner S, Ruppert J, Gabrysiak T G, Peters T H, Cox G, Richer, L, Martin, W J, and Scolaro, M J, *Inhibition of human immunodeficiency virus-*1 *proliferation by liposome-encapsulated sense DNA to the* 5' *TAT splice acceptor site*, Antisense Res Develop 2:187-197 [1992]; Laverman P, Boerman O C, Oyen W J G, Carstens F H M, Storm G, *In vivo applications of PEG liposomes: unexpected observations*, Crit Rev Ther Drug Carrier Syst 18(6): 551-66 [2001]; Oussoren C, Storm G, *Liposomes to target the lymphatics by subcutaneous administration*, Adv Drug Deliv Rev 50(1-2):143-56 [2001]; Bestmsn-Smith J, Gourde P, Desormeaux A, Tremblay M J, Bergeron M G, *Sterically stabilized liposomes bearing anti-HLA-DR antibodies for targeting the primary cellular reservoirs of HIV-I*, Biochim Biophys Acta 1468(1-2):161-74 [2000]; Bestman-Smith J, Desormeaux A, Tremblay M J, Bergeron M G, *Targeting cell free HIV and virally-infected cells with anti-HLA-DR immunoliposomes containing amphotericin B*, AIDS 14(16): 2457-65; Mayer L D, Hope M J, Cullis P R, *Vesicles of variable sizes produced by a rapid extrusion procedure*, Biochim Biophys Acta 858: 161-168 [1986]; Kinman, L. et al., *Lipid-drug associations enhanced HIV protease inhibitor indinovir localization in lymphoid tissues and viral load reduction: a proof of concept study in HIV-infected macaques*, J AIDS; 34:387-97 [2003]; Harvie P, Desormeaux A, Gagne N, Tremblay M, Poulin L, Beauchamp D, Bergeron 20 MG, *Lymphoid tissues targeting of liposome-encapsulated* 2',3'*-dideoxyinosine*, AIDS; 9:701-7 [1995]; U.S. Pat. Nos. 5,773,027; 5,223,263; WO 96/10399 A1).

Some useful methods of liposome preparation include extrusion, homogenization, remote loading, and reversed-phase evaporation. In extrusion, a lipid film composed of phospholipids only, or in combination with cholesterol and/or other additives, is formed by evaporating the organic solvent (such as chloroform) from the lipid solution. Hydrophobic drugs are added to the lipid solution prior to solvent evaporation. For entrapment of water soluble drugs, the dry lipid film is hydrated with and isotonic aqueous solution containing the drug by agitation (ultrasound, vortex, motorized stirrer, etc.). The lipid suspension is frozen and thawed 3-4 times. The suspension is then passed through a series of polycarbonate filters containing pores of a defined diameter, such as 0.8 μm, 0.4 μm, 0.2 μm, or 0.1 μm. For water soluble drugs, unencapsulated drugs are removed by gel permeation column chromatography, dialysis or diafiltration. The liposomes can be sterile-filtered (e.g., through a 0.22-μm filter).

A cryoprotectant, such as lactose, glucose, sucrose, trehalose or maltose can be added to the sterile liposomes as long as isotonicity is maintained. The liposomes can then be frozen and lyophilized and stored indefinitely as a lyophilized cake (e.g., Mayer L D, Hope M J, Quills P R, *Vesicles of variable sizes produced by a rapid extrusion procedure*, Biochim Biophys Acta 858: 161-168 [1986]; Tsvetkova N M et al., *Effect of sugars on headgroup mobility in freeze-dried dipalmitoylphosphatidylcholine bilayers: solid-state* 31*P NMR and PIIR studies*, Biophys J 75:

2947-2955 [1998]; Crowe T H, Oliver A E, Hoekstra F A, Crowe L M, *Stabilization of dry membranes by mixtures of hydroxyethyl starch and glucose: the role of vitrification*, Cryobiology 35: 20-30; Sun W Q, Leopold A C, Crowe L M, Crowe 114, *Stability of dry liposomes in sugar glasses*, Biophys J 70: 1769-1776 [1996]).

Homogenization is suited for large scale manufacture. The lipid suspension is prepared as described above. Freeze and thaw steps on a large scale may be a problem. The diameter of the liposomes is reduced by shooting the lipid suspension as a stream either at an oncoming stream of the same lipid suspension (microfiuidization) or against a steel plate (gualini7ation). This later technology has been used by the dairy industry for homogenization of milk Untrapped water-soluble drugs are removed by diafiltration Hydrophobic drugs are completely entrapped and there usually is no free drug to be removed (e.g., Paavola A, Kilpelainen I, Yliruusi J, Rosenberg P, *Controlled release injectable liposomal gel of ibuprofen for epidural analgesia*, Int J Pharm 199: 85-93 [2000]; Zheng S, Zheng Y, Beissinger R L, Fresco R, *Liposome-encapsulated hemoglobin processing methods*, Biomater Artif Cells Immobilization Biotechnol 20: 355-364 [1992]).

Another method of drug entrapment is remote loading. The drug to be entrapped must carry a charge. The degree of protonation or deprotonation is controlled by the pK of the ionizable group. A conjugate acid or base is trapped inside the liposomes. The ionizable drug is added to the outside of the liposomes. The pH is dropped such that the drug serves as a neutralizing salt of the ionizable substance trapped inside the liposomes. Due to the change in pH, the counter-ion to the entrapped ionizable molecule can diffuse out of the liposomes. This creates a gradient with sufficient energy to cause the drug to diffuse into the liposomes. An example is the loading of doxorubicin into preformed liposomes.

In reverse phase evaporation, a lipid film is solubilized in diethylether to a final concentration of typically about 30 mM. Typically, one part water with entrapped drug is added to three parts ether lipid solution. Energy in the form of sonication is applied forcing the suspension into a homogeneous emulsion. After a stable emulsion has been formed (which does not separate when resting for 1-3 h), the ether is removed by evaporation, typically yielding liposomes with about a 200 nm diameter and a high trapping efficiency.

Ethanol/calcium liposomes for DNA entrapment, typically yielding liposomes 50 nm in diameter, are prepared by any of the above methods (extrusion, homogenization, sonication). The liposomes are mixed with plasmid DNA, or linear DNA fragments, plus 8 mM calcium chloride. Typically, ethanol is added to the suspension to yield a concentration of about 40%. The ethanol is removed by dialysis and the resultant liposomes are generally less than 200 nm in diameter with about 75% of the DNA entrapped in the liposomes.

For cellular targeting, in accordance with the present invention, liposomes can be prepared by any of the above methods. The liposomes can contain a lipid to which proteins can be crosslinked. Examples of these lipids are: N-glutaryl-phosphatidylethanolamine, N-succinylphospatidyethanolamine, maleimido-phenyl-butyryl-phosphatidylethanolamine, succinimidyl-acetylthioacetate-phosphatidylethanolamine, SPDP-phosphatidlyethnaolamine. The glutaryl and succinimidyl phosphosphatidylethanolamine can be linked to a nucleophile, such as an amine, using cyclocarbodiimide. The maleimido, acetylthioacetate and SPDP phosphatidylethanolamines can be reacted with thiols on the proteins, peptides or small molecular weight ligands of <1000 g/mol. The protein can be derivatized to the liposomes after formation. Underivatized protein can be removed by gel permeation chromatography. Peptides and low molecular weight ligands can be derivatized to the lipids and added to the organic lipid solution prior to formation of the lipid film.

In accordance with the present invention, examples of useful lipids include any vesicle-forming lipid, such as, but not limited to, phospholipids, such as phosphatidylcholine (hereinafter referred to as "PC"), both naturally occurring and synthetically prepared phosphatidic acid (hereinafter referred to as "PA"), lysophosphatidylcholine, phosphatidylserine (hereinafter referred to as "PS"), phosphatidylethanolamine (hereinafter referred to as "PE"), sphingolipids, phosphatidyglycerol (hereinafter referred to as "PG"), spingomyelin, cardiolipin, glycolipids, gangliosides or cerebrosides and the like used either singularly or intermixed such as in soybean phospholipids (e.g., Asolectin, Associated Concentrates). The PC, PG, PA and PE can be derived from purified egg yolk and its hydrogenated derivatives.

Optionally, other lipids such as steroids, different cholesterol isomers, aliphatic amines such as long-chained aliphatic amines and carboxylic acids, long-chained sulfates, and phosphates, diacetyl phosphate, butylated hydroxytoluene, tocopherols, retinols and isoprenoid compounds can be intermixed with' the phospholipid components to confer certain desired and known properties on the formed vesicles. In addition, synthetic phospholipids containing either altered aliphatic portions such as hydroxyl groups, branched carbon chains, cycloderivatives, aromatic derivatives, ethers, amides, polyunsaturated derivatives, halogenated derivatives or altered hydrophilic portions containing carbohydrate, glycol, phosphate, phosphonate, quarternary amine, sulfate, sulfonate, carboxy, amine, sulfhydryl or imidazole groups and combinations of such groups can be either substituted or intermixed with the above-mentioned phospholipids and used in accordance with the invention. Some of these components are known to increase liposomal membrane fluidity, thus entailing more efficacious uptake, others are known to have a direct effect on, e.g., tumor cells by affecting their differentiation potential. It will be appreciated from the above that the chemical composition of the lipid component prepared by the method of the invention can be varied greatly without appreciable diminution of percentage drug capture, although the size of a vesicle can be affected by the lipid composition.

Saturated synthetic PC and PG, such as dipalmitoyl can also be used. Other amphipathic lipids that can be used, advantageously with PC, are gangliosides, globosides, fatty acids, stearylamine, long-chained alcohols and the like. PEGylated lipids, monoglycerides, diglycerides, triglycerides can also be included. Acylated and diacylated phospholipids are also useful.

By way of further example, in some embodiments, useful phospholipids include egg phosphatidylcholine ("EPC"), dilauryloylphosphatidylcholine ("DLPC"), dimyristoylphosphatidylcho ("DOPC"), dipalmitoylphosphatidylcholine ("DPPC"), distearoylphosphatidylcholine ("DSPC"), 1-myristoyl-2-palmitoylphosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2.-pabnitoyl phosphatidylcholine ("SPPC"), dioleoylphosphatidylycholine ("DOPC"), dilauryloylphosphatidylglycerol ("DLPG"), dimyristoylphosphatidylglycerol ("DMPG"), dipalmitoylphosphatidylgly cerol ("DPPG"), distearoylphosphatidylglycerol ("DSPG"), distearoyl sphingomyelin ("DS SP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), and dipalmitoyl sphingomyelin. ("DPSP").

In one embodiment, phosphatidylcholine and cholesterol are employed. However, any suitable molar ratio of non-steroidal lipid to steroidal lipid (e.g., cholesterol) can optionally be employed to promote the stability of a particular lipid-drug complex during storage and/or delivery to a mammalian subject.

Mixing the drug and lipids can be by any useful known technique, for example, by sonication, vortexing, extrusion, microfluidization, homogenization, use of a detergent (later removed, e.g., by dialysis). The drug and lipid are mixed at a lipid-to-drug molar ratio of about 3:1 to about 100:1 or higher which is especially useful for drugs that are relatively more toxic, and more preferably of about 3:1 to about 10:1, and most preferably of about 5:1 to about 7:1.

For some drugs, the use of an organic solvent can facilitate the production of the lipid-drug complex, such as a liposome. After mixing of the drug and lipids, the organic solvent is removed by any suitable known means of removal, such as evaporating by vacuum, or by the application of heat, for example by using a hair dryer or oven, or hot ethanol injection (e.g., Deamer, U.S. Pat. No. 4,515,736), as long as the lipid and drug components are stable at the temperature used. Dialysis and/or chromatography, including affinity chromatography, can also be employed to remove the organic solvent. Hydrating the drug is performed with water or any biocompatible aqueous buffer, e.g., phosphate-buffered saline, HEPES, or TRIS, that maintains a physiologically balanced osmolarity. Liposome rehydration can be accomplished simultaneously by removing the organic solvent or, alternatively, can be delayed until a more convenient time for using the liposomes (e.g., Papahadjopoulos et al., U.S. Pat. No. 4,235,871). The shelf life of re-hydratable ("dry") liposomes is typically about 8 months to about a year. This time span can be increased by lyophilization.

In one embodiment, the lipid-drug complex is a nnilamellar liposome. Unilamellar liposomes provide the highest exposure of drug to the exterior of the liposome, where it may interact with the surfaces of target cells. However, multilamellar liposomes can also be used in accordance with the present invention. The use of PEGylated liposomes is also encompassed within the present invention.

The lipid-drug complex further comprises an outer surface comprising at least one targeting ligand that specifically binds a marker on the surface of the immune cell. Examples of targeting ligands include antibodies that specifically bind the marker of interest, such as anti-CD209/DC-SIGN-specific antibodies, or anti-CD4, anti-CD45RO, or anti-HLA class IL "Antibodies" include whole antibodies as well as antibody fragments, with a specific target-binding capability of interest, ie., antigen-specific or hapten-specific targeting ligands. Antibody fragments include, for example Fab, Fab', F(ab')$_2$, or F(v) fragments. Antibodies can also be polyclonal or monoclonal antibodies. Antibodies also include antigen-specific or hapten-specific targeting ligands complexed with lipid-soluble linker moieties. In some embodiments, antibodies are coupled to the lipid-drug complex, such as a liposome-drug complex, via protein A of the Staphylococcus-aureus type, or via protein G which is typical of some other bacterial species.

Optionally, the lipid-drug complex further comprises one or more biomembrane components that can further enhance the specific (i.e., active) targeting ability, cytotoxicity, or other therapeutic parameter of the liposome. Such biomembrane components include a membrane-associated protein, an integral or transmembrane protein (e.g., a glycophorin or a membrane channel), a lipoprotein, a glycoprotein, a peptide toxin (e.g., bee toxin), a bacterial lysin, a Staphylococcus aureus protein A, an antibody, a specific surface receptor, or a surface receptor binding ligand. The use of specific vector molecules coupled to, or embedded within a liposomal surface, is also encompassed within the present invention for enhanced transmembrane delivery and uptake of liposome-encapsulated compounds that otherwise are only insufficiently delivered to or into a cell, or that are not efficiently delivered to a specifically desirable intracellular organelle (e.g., as reviewed in: Torchilin V P, Lukyanov A N, *Peptide and protein drug delivery to and into tumors: challenges and solutions*, Drug Discov Today 2003 Mar. 15; 8(6):259-66; Sehgal A, *Delivering peptides and proteins to tumors*, Drug Discov Today 2003 Jul. 15; 8(14): 619; Koning G A, Storm G, *Targeted drug delivery systems for the intracellular delivery of macromolecular drugs*, Drug Discov Today 2003 Jun. 1; 8(11):482-3). Such vector molecules can include so-called protein transduction domains (PTDs) which are derived from various viruses or from Drosophila antennapedia. For application in HIV disease, the HIV Tat protein, or a derivative or fragment that acts as a PTD, is also useful (e.g., Schwarze, S. R., et al., In vivo protein transduction: delivery of a biologically active protein into the mouse, Science 285:1569-72 [1999]).

The lipid-drug complex, such as a liposome, is preferably, but not necessarily, about 30 to about 150 nanometers in diameter, and more preferably about 50 to about 80 nanometers in diameter.

In accordance with the present invention, the lipid-drug complexes can be preserved for later use by any known preservative method, such as lyophili 7ation (e.g., Crowe et al., U.S. Pat. No. 4,857,319). Typically, lyophilization or other useful cryopreservation techniques involve the inclusion of a cryopreservative agent, such as a disaccharide (e.g., trehalose, maltose, lactose, glucose or sucrose).

The lipid-drug complex, e.g., a liposome, is administered to a subject by any suitable means such as, for example by injection. Administration and/or injection can be intrarterial, intravenous, intrathecal, intraocular, intradermal, subcutaneous, intramuscular, intraperitoneal, or by direct (e.g., stereotactic) injection into a particular lymphoid tissue, or into a tumor or other lesion. Introduction of the lipid-drug complex into lymphatic vessels, preferably, is via subcutaneous or intramuscular injection.

In accordance with the present invention, "lymphoid tissue" is a lymph node, such as an inguinal, mesenteric, ileocecal, or axillary lymph node, or the spleen, thymus, or 30 mucosal-associated lymphoid tissue (e.g., in the lung, lamina propria of the intestinal wall, Peyer's patches of the small intestine, or lingual, palatine and pharyngeal tonsils, or Waldeyer's neck ring).

Injection can also be by any non-intravenous method that drains directly, or preferentially, into the lymphatic system as opposed to the blood stream. Most preferred is subcutaneous injection, typically employing a syringe needle gauge larger than the lipid-drug complex. Intraperitoneal injection is also useful. Typically, injection of the injectate volume (generally about 1-5 cm³) is into the subject's arm, leg, or belly, but any convenient site can be chosen for subcutaneous injection. Because drug subcutaneously administered, in accordance with some embodiments of the present invention, enters the lymphatic system prior to entering systemic blood circulation, benefits include 1) Distribution throughout the lymphoid system and localization in lymph nodes; and 2) Avoiding or minimising of protein-mediated destabilization of lipid-drug complexes.

Typically, in treating HIV/AIDS, the frequency of injection is most preferably once per week, but more or less (e.g., monthly) frequent injections can be given as appropriate.

Accordingly, the present invention facilitates a treatment regimen that can involve a convenient weekly injection rather than multiple drug doses daily, as practiced typically 20 in current AIDS treatment regimes. This feature may lead to improved patient compliance with the full course of treatment for some individual patients.

While the invention has been described with reference to its preferred embodiments, it will be appreciated by those skilled in this art that variations can be made departing from the precise examples of the methods and compositions disclosed herein, which, nonetheless, embody the invention.

EXAMPLES

Example 1. Materials and Methods

Preparation of Liposomes.

A 30 μmol lipid film composed of DOPC/Chol/DOPE-MBP (36.5:33.0:2.5 mol:mol:mol) was formed (cholesterol was purchased from Calbiochem, San Diego, Calif., USA; and DOPE and DOPE-MPB were from Avanti Polar Lipids, Alabaster, Ala., USA). Lipid films were hydrated with 1 ml 50 mM calcein (Molecular Probes, Eugene, Oreg., USA) in PBS (pH 7.0), sonicated in a bath sonicator (5 min) and extruded ×5 through a 0.1 μm nucleopore filter (Avanti Polar Lipids) using a hand-held extruder. Also, freeze-thaw cycles can be employed. The mean liposome size was determined by quasielectric light scattering with a Nicomp 380 ZLS Zeta-Potential Particle Sizer (Particle Sizing Systems, Santa Barbara, Calif., USA), yielding an average diameter of 146.7±31.0 nm.

Protein a Liposomes.

To be able to test the targeting ability of different antibodies with a standardized liposome, immunoglobulin-molecules were coupled to liposomes via protein A of Staphylococcus aureus. Protein A is a bacterial cell wall component consisting of a single polypeptide chain of molecular weight 42 IcDa. Protein A has the ability to specifically bind to the Fc region of immunoglobulin molecules, especially IgG. One protein A molecule can bind at least 2 molecules of IgG simultaneously (Syiquist J, Meloun B, Hjelm H, *Protein A isolated from Staphylococcus aureus after digestion with lysostaphin*, Eur J Biochem 29: 572-578 [1972]). Protein A bearing liposomes were formed and their functionality in binding antibody-molecules was tested. Targeting of DC-SIGN and other membrane markers was achieved with Protein A liposomes pre-incubated with established antibody concentrations of either of several DC-SIGN-specific mAbs (all IgG1κ isotype), or irrelevant IgG1κ control mAb (MOPC-21/P3), or anti-bodies specific for the other membrane markers.

Protein A was derivatized with succinimidylacetyl-thioacetate (SATA, Pierce Biotechnology, Rockford, Ill., USA) at a molar ratio of 10:1 SATA to protein in PBS, pH 9.0 for 1 h. Unreacted SATA was removed from the protein A using a Sephadex G-25 superfine spin column equilibrated with PBS (pH=7.4). The thiol protecting group was removed by incubating the derivatized protein A with 0.2 ml 0.5 M $NH_2OH$ (Sigma), 0.5 M HEPES (pH=7.4) and 25 mM EDTA (Fisher) for 15 min. Reactants were removed and buffer was changed using a second G-25 Sephadex spin column equilibrated with PBS (pH=6.5). At the same time, the calcein-containing liposomes were also centrifuged through a Sephadex spin column equilibrated with PBS (pH=6.5) to remove untrapped calcein. The derivatized protein A was immediately added to the liposomes at a molar ratio of 100 lipid to protein. After 2-h incubation at RT, the liposome×protein A conjugate was separated from free protein a using a sepharose CL-4B column equilibrated with PBS. The number of thiols/protein A was verified by their reaction with 2 mM 5,5'-dithio-bis(2-nitrobenzoic acid) (Aldrich, Milwaukee, Wis., USA). As a measure for calcein encapsulation efficiency and liposomal stability, the quenching (Q) [%] of the pooled preparation in absence and presence of Triton Tx-100 was determined according to:

$$Q = \frac{(\text{Pool} + Tx\text{-}100)_{OD\,280\,NM} - (\text{Pool} - Tx\text{-}100)_{OD\,280\,NM}}{(\text{Pool} + Tx\text{-}100)_{OD\,280\,NM}} \times 100 [\%] \qquad (I)$$

Typically, Q≈80% indicated that leakage of calcein was insignificant.

Immunoliposomes and Antibodies.

Calcein-entrapping protein A liposomes were stored at 4° C. in the dark and used for up to 3 months. Immunoliposomes were prepared by incubation for 30 min at RT of protein A liposomes with test monoclonal antibodies (mAb; see below) or irrelevant negative control IgG (mAb MOPC-21/P3; eBioscience, San Diego, Calif., USA); Reeves, L P et al., Anti-Leu3a induces combining site-related anti-idiotypic antibody without inducing anti-HIV activity, AIDS Res Hum Retroviruses 7:55-63 [1991]) at a 5:1 molar ratio of mAb:protein A. The molar ratio of lipid to protein A was approximately 1000. Unbound antibody could be removed with magnetic Protein A beads (New England Biolabs, Beverly, Mass., USA). However, no significant effect on cell labeling was observed.

Monoclonal antibody binding to protein A liposomes was tested by Ficoll flotation. Specifically, antibodies were incubated with liposomes (30 min, RT) at the mAb:lipid ratio used for cell labeling. Polyclonal rabbit anti-mouse Ab×alkaline phosphatase (AP) was added to the incubation. The mixture was made from 20% ficoll 400 using a 30% Ficoll stock in PBS with a final volume of 0.4 ml, transferred to a microfuge tube, and 0.4 ml of 10% ficoll/PBS was layered on top and subsequently added a 0.4-ml layer of PBS. Tubes were centrifuged at 15,000 rpm for 15 min at RT. The PBS/10% ficoll interface was assayed for AP activity. Incubation with secondary Ab×AP yielded a 10-fold lower activity than incubation with primary mAb and secondary antibody, indicating that primary mAb had bound to protein A on the liposomes (results not shown).

In order to identify an mAb ensuring maximal efficacy for targeting of DC-SIGN, protein A liposomes were preincubated with either of three different CD209-specific mAbs derived from clones 120507 (IgG2b), 120526 (IgG2a) (R&D Systems, Minneapolis, Minn., USA) and DCN46 (1gG1x) (BD Biosciences, San Jose, Calif., USA). Targeting with mAb 120507 turned out superior, and the results described herein have exclusively been obtained with this antibody. Further antibodies for phenotyping (employed as primary mAbs) and for generating immunoliposomes were specific for CD1a (BL6; Coulter Immunotech, Miami, Fla., USA), CD4 (SIM.4) (NIH/McKesson; cf. Acknowledgments), CD14 (UCHM-1), CD45R0 (UCHL1) and CD83 (H1315a17.11) (all from Serotec, Oxford, UK).

Cellular Binding/Uptake Studies.

Mature cells were harvested on day 7 of culture by pelleting non-adherent veiled cells from the supernatants and detaching weakly adherent cells with 1% EDTA in PBS for 30 min at 4° C.; strongly adherent cells were obtained by gently applying a cell scraper (TPP). All fractions were pooled, washed with PBS and kept in medium 80/20 plus 1% PBS on ice until used. For testing, cells were plated in fresh culture medium with 1% FBS at a density of $2 \times 10^5$ cells/well. To obtain the time-dependency of the targeting to dendritic cells, the $2 \times 10^5$ MoDCs per well or onset in the same medium were incubated with liposomes at 50 μM lipid at 37° C. for 1, 3 and 24 hours or other times and temperatures, as described hereinbelow. After incubation the cells were washed three times with phosphate-buffered saline (PBS, pH 7.2; without bivalent cations) and analysed by fluorescence activated cell sorting (FACS; i.e., "flow cytometry," see below). In all the experiments, the liposome-to-cell-ratio was constant.

Flow Cytometry.

Flow cytometry can be employed: (1) to determine the phenotypes of My-DCs and T-cells at different times throughout DC differentiation and DC/T-cell co-culture (i.e., mixed leukocyte cultures or antigen-specific stimulation) with or without the DCs being infected with select M- and/or T-tropic strains of HIV-1, and/or treated with DC-SIGN-specific or control liposomes; and (2) to determine co-delivery of calcein/drug(s) to infected My-DCs or, more specifically, infected MoDCs. Labeled MoDCs were analyzed on a Coulter Epics XL-MCL (Beckman Coulter, Fullerton, Calif.) flow cytometer according to the manufacturer's instructions, immediately after indirect staining with (i) primary mAbs and secondary polyclonal IgG conjugated with fluorescein-5-isothiocyanate (1411C) (eBioscience) (Gieseler, R et al., *In-vitro differentiation of mature dendritic cells from human blood monocytes*, Dev. Immunol 6:25-39 [1998]), (ii) incubation with the respective calcein-containing immunoliposomes, or (iii) negative controls. Flow cytometry was performed; only gated cells were evaluated for antigen expression, as well as for liposomal targeting and uptake studies. Briefly, cells were gated via forward and side scatter dot plotting to exclude debris. Histograms were established for gated cells, as suitable for FITC and calcein, i.e. $\pi_{EX}$=488 nm and $\pi_{EM}$=525 nm. Data were downloaded, and the corresponding histograms for test samples and controls were overlaid and analyzed with WinMDI 2.8 software (J. Trotter; facs.scripps.edu). Targeting efficacy was determined directly after incubating DCs (or, when employed, macrophages) with the respective liposome/Protein A/mAb construct, or with liposomal negative controls employing the irrelevant isotype control antibody MOPC-21/P3. Results of negative controls employing protein A liposomes not loaded with mAbs were identical to those obtained with irrelevant control IgG. An influence via non-specific uptake of liposomes by MyDCs could thus be excluded.

Targeting Efficacy of Immunoliposomes.

To determine expression of a given marker by a specific mAb, its efficient mean fluorescence intensity ($AMFI_{mAb}$) was calculated as the difference of its measured MFI ($MFI_{mAb}$) and the MFI measured for negative control IgG ($MFI_{Co-IgG}$), i.e.

$$\Delta MFI_{mAb} = MFI_{mAb} MFI_{Co-IgG} \quad (II)$$

and expressed as the percentage of MyDCs expressing this marker ($MyDC_{mAb}^+[\%]$).

To determine the uptake of a given mAb-loaded immunoliposome inAb), ($ILS_{mAb}$), its efficient MFI ($\Delta MFI_{ILS}$) resulted from the difference of its measured MET ($MFI_{ILS-mAb}$) and the MFI obtained for the immunoliposome negative control ($MFI_{ILS-Co-IgG}$), i.e.

$$\Delta MFI_{ILS} = MFI_{ILS-mAb} MFI_{Co-IgG} \quad (III)$$

thus providing the percentage of immunoliposome-positive MyDCs ($MyDC_{ILS}^+[\%]$).

Marker expression and immunoliposomal binding and uptake do not necessarily correlate. For instance, while clearly expressing a given antigen when identified with a specific mAb, interaction of the same antigen with the much larger immunoliposomes labeled with the same mAb specificity may lead to shedding of the surface marker, which will result in a loss of signal fluorescence. Based on Equations (II) and (III), the immunoliposomal net targeting efficacy (TEms) was thus determined as $$TE_{ILS} = \frac{MyDC_{ILS} \times 100}{MyDC_{mAb}}[\%] \quad (IV)$$

wherein a result close to 100% indicates similar binding of an mAb and its corresponding immunoliposome; a lower result indicates loss of signal upon liposomal engagement; and a result clearly above 100% shows accumulation of liposomally delivered fluorophore, hence suggesting active uptake of the respective type of immunoliposome. Equation (IV) is easily transformed for the relative fluorescence of immunoliposomes vs. fluorescently labeled mAbs (RFics), $$RF_{ILS} = \frac{MyDC_{ILS} \times 100}{MyDC_{mAb}} - 100[\%] \quad (V)$$

wherein negative results indicate a loss, and positive results a gain, in signal fluorescence.

Peripheral Blood Leukocytes (PBL).

Mononuclear leukocytes (MNLs) and/or T-cells were prepared as described before (Gieseler, R, et al., *In-vitro differentiation of mature dendritic cells from human blood monocytes*, Dev. Immunol. 6:25-39 [1998]). Briefly, MNLs were enriched from whole blood diluted 1:1 with phosphate-buffered saline (PBS) without $Ca^{2+}/Mg^{2+}$ (Cambrex, Walkersville, Md., USA) by density gradient centrifugation over Lymphoprep ($\rho$=1.077 g/cm$^3$; Nyegaard, Oslo, Norway). Buffy coats were harvested and pooled, and residual platelets were removed by 3-4 washes with PBS. These procedures involved several 10-min centrifugation steps at 260×g and 4 degrees C.

Magnetic-Activated Cell Separation (MACS) of Monocytes, CD4$^+$ and CD8$^+$ T Cells.

Monocytes were isolated via negative magnetic-activated cell separation (MACS; Miltenyi, Bergisch-Gladbach, Germany and Auburn, Calif., USA) by removing CD3$^+$, CD7$^+$, CD19$^+$, CD45RA$^+$, CD56$^+$ and mIgE$^+$ cells with mAb-coated magnetic microbeads. Negative monocyte separation had been chosen to avoid cell activation and was performed according to the manufacturer's instructions. Briefly, the procedure involved 2 washes with PBS supplemented with 0.5% bovine serum albumin (BSA; cell-culture grade, <0.1 ng/mg endotoxin; ICN, Irvine, Calif., USA) and 2 mM EDTA (Sigma, St. Louis, Mo., USA), and the washed cells were passed through an LS magnetic microcolumn placed in a defined magnetic field (Miltenyi), thus enriching the monocytes to 98.6-99.9% purity (range of n=3), as determined by flow cytometry for CD14.

Differentiation of Myeloid Dendritic Cells.

Mature and immature MyDCs were generated from peripheral blood monocytes. Briefly, monocytes were isolated by successive density gradient centrifugation of PBS-diluted whole blood over Lymphoprep ($\rho=1.077$ g/cm$^3$) (Nyegaard, Oslo, Norway) and, successively, by negative magnetic cell separation (MACS), in accordance with the manufacturer's instructions (Miltenyi). Monocytes were then seeded at $1\times10^5/200$ µl in 96-well microtiter plates (TPP, Trasadingen, Switzerland). According to two generally accepted protocols, we differentiated two different phenotypes of functionally competent DCs. Both protocols employed granulocyte/macrophage colony-stimulating factor (GM-CSF), and interleukin 4 (IL-4) as basic DC differentiation factors, thus leading to an immature, antigen-capturing DC stage (Peters J H, Xu H, Ruppert J, Ostermeier D, Friedrichs D & Gieseler R K, *Signals required for differentiating dendritic cells from human monocytes in vitro*, Adv Exp Med Biol; 329:275-80 [1993]; Ruppert J, Schutt C, Ostermeier D & Peters J H, *Down-regulation and release of CD14 on human monocytes by IL-4 depends on the presence of serum or GM-CSF*, Adv Exp Med Biol; 329:281-6 [1993]).

Mature antigen-presenting DCs were then obtained by adding tumor-necrosis factor (TNF)-a, leading to a DC type able to initiate both T-helper (Th)1- and Th2-dependent immunity (Caux C, Dezutter-Dambuyant C, Schmitt D & Banchereau J, GM-CSF and TNF-α cooperate in the generation of dendritic Langerhans cells, Nature; 360:258-61 [1992]; Sallusto F & Lanzavecchia A, *Efficient presentation of soluble antigen by cultured human dendritic cells is maintained by granulocyte/macrophage colony-stimulating factor plus interleukin 4 and downregulated by tumor necrosis factor alpha*, J Exp Med; 179:1109-18 [1994]; Banchereau J & Steinman R M, *Dendritic cells and the control of immunity*, Nature; 392:245-52 [1998]).

Alternatively, mature DCs were generated in presence of interferon (IFN)-γ (Gieseler R, Heise D, Soruri A, Schwartz P & Peters J H, *In-vitro differentiation of mature dendritic cells from human blood monocytes*, Develop Immunol; 6:25-39 [1998]). Such DCs appear to primarily induce Th1 cells, thus activating cytotoxic T-cells eliciting anti-tumor immunity (Soruri, A. et al., *Specific autologous anti-melanoma T cell response in vitro using monocyte-derived dendritic cells*, Immunobiology; 198:527-38 [1998]) and, presumably, antiviral immune responses, due to MEIC class I-restricted antigen presentation. In most cases, DCs were differentiated for 7 days. However, DCs were kept for up to 21 days in select experiments. All differentiation factors were obtained from Sigma (St. Louis, Mo., USA).

DC Harvesting and Liposome Incubation.

Harvested MyDCs and liposome preparations were incubated at differing relative concentrations (depending on the experimental context) for 3 hours at room temperature, followed by genotypic, phenotypic and functional (PCR, flow cytometry, ELISA, mixed leukocyte culture and stimulation for recall antigens) evaluation. Mature non-adherent and adherent DCs were harvested on day 7.

First, the differentiation medium was collected, centrifuged, and the pelleted DC fraction of non-adherent veiled cells was harvested. Second, adherent DCs were detached from the wells by incubating them with PBS/EDTA for 30 min at 4° C., and by successively employing a rubber policeman. Detached adherent DCs were pooled with the non-adherent fraction, adjusted to the cell numbers and incubated with the liposome concentrations indicated for each experiment.

As described above, myeloid dendritic cells obtained by protocols employing TNF-α or IFN-γ, were analyzed flow-cytometrically for expression of CD1a, CD4, CD14, CD40, CD45RA, CD45RO, CD68, CD69, CD83, CD184, CD195, CD206, CD207, CD208, and/or CD209 (i.e., DC-SIGN) with mouse anti-human IgG1κ mAbs (MOPC-21/P3 as control). Depending on whether only one or two mAbs were employed, antigens were either stained directly with Fil C-, PE-, or PCS-labeled antibodies, or were stained indirectly with unlabeled first mAbs plus secondary polyclonal IgG× FITC (available from eBioscience).

MOPC-21/P3 was employed as the IgGlx isotype controL Results served three purposes, i.e.

(a) To verify that the cells differentiated in vitro exhibited genuine DC phenotypes, (b) To define their phenotypic and interindividual differences, and (c) To compare the expression of a given marker with the histogram pattern displayed after incubation with liposomes targeted by the same antibody.

Prior to DC targeting, and for each test onset, 20 jul anti-CD209 (DC-SIGN) and/or other antibody at working dilution were incubated with 30 ill liposomes on a rotator for 1 h at RT. Aliquots of cell suspension of at least $5\times10^4$ DCs (or, when employed, macrophages) were incubated with liposomes under saturating conditions for 3 h at RT under continuous agitation, and then examined by flow cytometry. (Tested conditions were 1 h, 3 h and 24 h. The most reliable and reproducible results were obtained by 3-h co-incubation.).

Hiv Strains.

HIV strains were obtained from the NM Repository (Rockville Pike, Bethesda, Md.), ie., M-(R5)tropic Ada-M and Ba-L; and T-(X4)tropic HX133, Lai, Lai/IIIB and HTLV-IIIB HIV strains were tested for their "tissue-culture 50% infective dosage" (TCID50) according to protocols known to the art. According to the TCID50 results, viral supernatants were diluted, aliquoted and frozen at −80° C. until employed for infection at different dose-infection kinetics.

Cryostorage of T Cells.

Separated CD4$^+$ or CD8$^+$ T cells, complete T cells, or total lymphocytes (comprising T and B cells) were stored individually or as pools from two to four donors (for allogeneic stimulation) at −80° C. or −196° C., according to methods known to the art. Such cells are thawed when needed for autologous or allogeneic mixed leukocyte cultures, or for recall antigen tests.

Liposomes and Antiviral Drugs.

For primary experimental purposes, liposomes were surface-labeled with Protein A so as to exchangeably bind antibodies specific for different antigens. These liposomes were entrapping calcein as a fluorescent tracer dye. To find a suitable drug targeting system, a range of single or combined drugs interfering with HIV propagation (e.g., Viread® [tenofovir], Retrovir [AZT], Epivir [3-TC], Zerit® [d4T], Videx® [didanosine], Emtriva® [emtricitabine], Sustiva® [efavirenz], Viramun® [nevirapine], -Rescriptor®

[delavirdine], Norvir® [ritonavir], Agenerase® [amprenavir], Hivid® [ddC], lopinavir, Kaletra® [lopinavir+ritonavir], Viracept® [nelfinavir], Crixivan® [indinovir sulfate], Fortovase® [saquinavir], Invirase® [saquinavir mesylate] and/or Atazanavir®), as well as other drugs that are still in the experimental phase of therapeutic research, can be employed to obtain proof of anti-HIV efficacy.

ELISA for HIV p24 Core Antigen.

Supernatants can be tested according to the manufacturer's instructions for presence of p24 by a commercially available ELISA (Abbott Laboratories).

Quantitative Polymerase Chain Reaction (qPCR) for HIV.

The degree of integration of HIV proviral DNA into dendritic-cell host DNA can be determined by using nested primer pairs (nested semi-qPCR) for HIV proviral sequences, such as the following:

```
Outer Primers:
                                        (SEQ ID NO: 1)
5'-ag t-ggg-ggg-aca-tca-agc-agc-cat-gca-aat-3' //

(SEQ ID NO: 2)
5'-tca-tct-ggc-ctg-gtg-caa-3' //

Inner Primers:
                                        (SEQ ID NO: 3)
5'-cag-ctt-aga-gac-cat-caa-tga-gga-agc-5g-3'
(5-FAM) //; this is a LUX-primer, labeled with
5-carboxyfluorescein, i.e., 5-FAM; "5" = 5-FAM).

(SEQ ID NO: 4)
5'-ggt-gca-ata-ggc-cct-gca-t-3'. //
```

Isolation of DNA can be accomplished according to manufacturer's instructions ("Easy-DNA-Kit", in protocol #3 "Small Amounts of Cells, Tissues, or Plant Leaves", Invitrogen). The PCR reaction mixture typically includes the following: Buffer (5 µl of 10×PCR Rxn Buffer, Invitrogen); $MgCl_2$ (3 µl of 50 mM $MgCl_2$, Invitrogen); dNTP (1µ of mixture of dATP, dCTP,dGTP,dTTP: 10 µM, each); Outer Primer (SEQ ID NO:1; 1 µl of 10 pmol/µl); Outer Primer (SEQ ID NO:2; 1 µl of 10 pmol/µl); Taq (0.2 µl of 5 Units/p.1, Platinum Taq DNA Polymerase, Invitrogen); double distilled water (37 µl); DNA sample (2 µl). One standard thermal cycling profile was the following: 5 min at 95° C.; (20 s at 95° C.; 30 s at 55° C.; 30 s at 72° C.)×25; 2 min at 72° C.; hold at 4° C. PCR is generally repeated using two microliters of amplified DNA transferred from the first reaction in fresh PCR reaction mixture, except using the inner primers (SEQ ID NO:3 and SEQ ID NO:4) instead of the outer primers, and employing a different thermal cycling profile: 5 min at 95° C.; (20 s at 95° C.; 30 s at 55° C.; 30 s at 72° C.)×35; 2 min at 72° C. (melting curve 95° C. down to 55° C. in steps of 0.5° C.).

In a given sample, DNA quantification can be achieved by comparison with a serial dilution of a DNA sample of known quantity of HIV proviral DNA. To allow quantifying HIV proviral DNA from samples with different contents of total cellular DNA (e.g., from dendritic cells), a Multiplex-PCR can be performed. Briefly, a second nested PCR can be performed in the same reaction, with a LUX primer labeled with 6-carboxy-4',5'-dichloro-2',7'-dirnethoxyfluorescein succini rn idyl ester, for a human chromosome sequence (genome equivalent). This permits quantification of the total DNA content per sample. Numbers of proviral copies per human genome equivalent can be calculated from such data.

Example 2. Active Targeting of Immune Cells with Monospecific or Bispecific Immunoliposomes Peripheral blood mononuclear cells (PBMNCs) were evaluated according to their size (forward scatter) and granularity (side scatter) and thus were gated as naïve T and B cells; activated T-cells and B-cells; and monocytes, including a small proportion of blood dendritic cells (data not shown). Cultured monocyte-derived dendritic cells (MoDCs) were tested for expression of markers delineating their developmental stage (maturity), as well as for DC subtype markers. The DCs expressed markers typical for skin and mucosal DC phenotypes that are considered to play a key role in HIV infection. When being infected via the mucosal route, mucosal DCs are the first immune cell type to be directly infected by HIV (and integrate its genetic information as proviral DNA) and/or harvest HIV on their surface by DC-SIGN and/or take up HIV by any of various mechanisms to retain it in intracytoplasmic compartments (e.g., endosomes, fused phago-endosomes, or phagolysosomes). Such cells then migrate to regional and local lymph nodes where passing on HIV to other cell types, most prominently T-helper cells (i.e., "CD4 cells") as well as other reservoir cells, including the next generation of lymph node-settling DCs. In considering all this, the DCs generated in our in-vitro system thus provide an ideal model for testing the presumptive targeting efficacy for such cells in vitro.

MoDCs matured by 7-day culture with GM-CSF, 1L-4 and subsequent TNF-α were tested by flow cytometry for expression of markers generally expressed by DCs or subpopulations thereof. Apart from DC-SIGN (CD-209), we chose markers delineating mature DCs in vitro and in vivo (CD40, CD45RO, CD83), as well as dendritic Langerhans cells of the epidermis (CD1a) and the intestinal (CD4) and nasal mucosa (CD14). Phenotyping thus served (i) for verifying MoDCs generated in vitro as mature; (ii) for proving strong expression of DC-SIGN (CD209) as the pre-conceived target for immunoliposomal compound delivery to MyDCs; (iii) for pinpointing further potential target antigens conforming to the requirement of consistent high expression; and (iv) for determining whether the generated MoDCs expressed CD 1a and/or CD14 as potential targeting structures expressed by epidermal and mucosal Langerhans cells in vivo.

Relative mean fluorescence intensities (AHED of test conditions vs. negative controls (n=3) characterized the phenotypic profile of mature MoDCs as $CD1a^{+++}$, $CD4^+$, $CD14^{\pm\ to\ +++}$, to $CD40^{++\ to\ +++}$, $CD45R0^{+\ to\ +++}$, $CD83^+$ and $CD209^{+++}$ [with: (−), test antibody congruent with negative control; (±), AMFI peak ≤×5 above negative control; (+), ΔMFI peak ≤×10 above negative control; and (+++), ΔMFI peak×≥250 negative control]. Of all markers tested, expression of CD14 varied most considerably among the donors. In contrast, DC-SIGN (CD209) and CD1a (a Langerhanscell marker) consistently revealed high expression in all donors examined.

FIG. 1 shows targeting of calcein-labeled liposomes to MoDCs mediated by DC-SIGN or other targeting ligands. Mature MoDCs were generated in vitro for 7 days. Liposomes were incubated with either one or two monoclonal antibodies (mAbs) specific for key markers expressed by MoDCs, so as to obtain monospecific liposomes (for CD 1a, CD83, or CD209) or bispecific liposomes (for CD1a+CD83, CD1a+CD209, or CD 83+CD209) (Zhou L T, Tedder T F, $CD14^+$ *blood monocytes can differentiate into functionally mature $CD83^+$ dendritic cells*, Proc Natl Acad Sci USA; 93(6):2588-92 [1996]; Gieseler R, Heise D, Soruri A, Schwartz P, Peters J R, *In-vitro differentiation of mature dendritic cells from human blood monocytes*, Develop Immunol.; 6(1-2):25-39 [1998]. Geijtnbeek T B, Torensma R, van Vliet S J, van Duijnhoven G C, Adema G J, van Kooyk Y, Figdor C G, *Identification of DC-SIGN, a novel*

*dendritic cell-specific ICAM-3 receptor that supports primary immune responses*, Cell; 100(5):575-85 [2000]; Geijtenbeek T B, Kwon D S, Torensma R, van Vliet S J, van Duijnhoven G C, Middel J, Cornelissen I L, Nottet H S, KewalRamani V N, Littman D R, Figdor C G, van Kooyk Y, *DC-SIGN, a dendritic cell-specific HIV-1-binding protein that enhances trans-infection of T cells*, Cell; 100(5):587-97 [2000]).

Best results were obtained when mature MoDCs were incubated with liposomes for 3 h at 37° C. under continuous gentle agitation. Employing the above-described protocol, further targeting variants now included CD1a and CD83 as potential targets expressed by Langerhans cells in the surface-forming tissues (Teunissen M B M, *Dynamic nature and function of epidermal Langerhans cells in vivo and in vitro: a review, with emphasis on human Langerhans cells*, Histochem. J. 24:697-716 [1992]), as well as mature intralymphoid MyDCs (Zhou L J, Tedder T F, *CD14+ blood monocytes can differentiate into functionally mature CD83+ dendritic cells*, Proc Natl Acad Sci USA 93:2588-92 [1996]; Gieseler R et al., In-vitro differentiation of mature dendritic cells from human blood monocytes, Dev Immunol 1998; 6:25-39 [1998]). The CD1a and CD83 markers turned out to be comparatively unlikely targeting structures. In contrast, targeting of DC-SIGN again showed high liposomal binding and uptake of the fluorochrome (FIG. 2).

Monoclonal antibodies (mAbs) and mAb-labeled immunoliposomes tested were specific for CD4, CD45RO and CD209 (DC-SIGN). Experiments showed the most favorable incubation time for mature MyDCs with immunoliposomes and investigated whether incubation with either one or two types of immunoliposomes (the latter at half the concentrations employed upon single targeting) might offer a decisive advantage. Binding of specific mAbs visualized with FITC-labeled secondary antibody (left-hand column) revealed the degree of antigen (Ag) expression. Mature MyDCs generated from the same donors were incubated for 1, 3 or 24 h with immunoliposomes at 37° C. [a preliminary experiment had proven 37° C. superior to 4° C. or RT (not shown)] (FIG. 1, right column). Flow-cytometric histograms for phenotyping or targeting (shaded curves) and negative controls (empty curves) revealed the best signal-to-noise ratio, most consistent uptake and highest reproducibility for 3-h incubation. Most intense staining was found for anti-CD209 and, secondarily, anti-CD45RO. Combination of both conditions had no substantial advantage over mono-specific targeting of DC-SIGN. As shown in FIG. 1, most efficacious targeting and delivery of liposomal contents was achieved with monospecific liposomal targeting of CD209 (DC-SIGN). When the targeting efficacies of mAbs only and LS-coupled mAbs were compared, it was apparent that liposomal delivery led to increased (intra)cellular fluorescence. It was shown that liposomal delivery of calcein led to a right shift compared to antibody-conjugated FITC.

Figure 2:
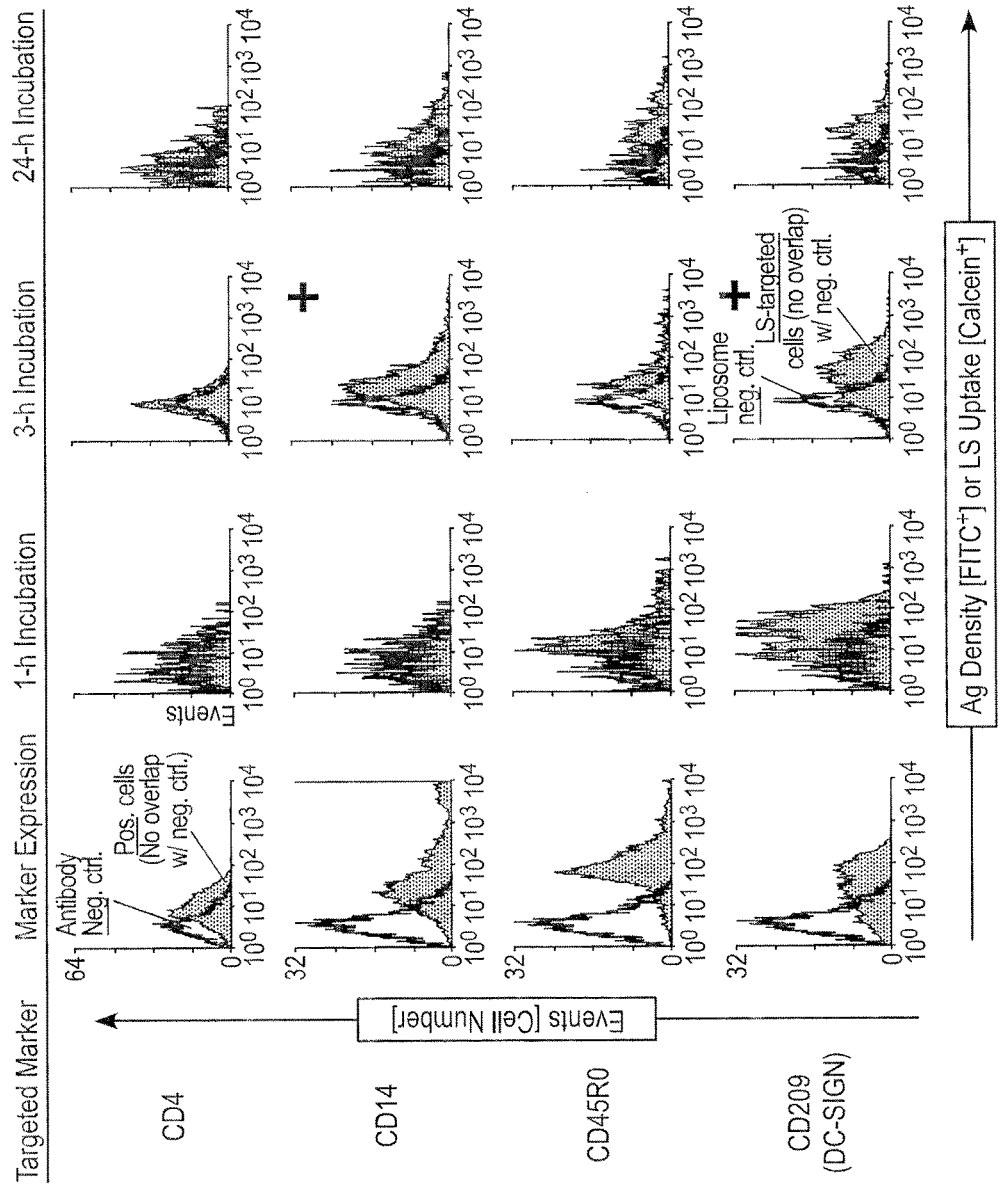
FIG. 2 shows monospecific liposomal targeting with respect to kinetics and efficacy. Mature MoDCs were generated according to protocol described herein and investigated for uptake of different constructs of targeted protein A liposomes furnished with mAbs directed against CD4, CD14, CD45R0 or CD209. The MoDCs were co-incubated with the liposomes for 1, 3 or 24 h and then harvested and tested by flow cytometry. Control mAbs were used to detect cellular surface expression of the respective antigens (column headed "Marker Expression"). Empty curves indicate isotype controls; shaded curves indicate test conditions. The two panels bearing bold crosses show the highest mean fluorescence intensities, indicating the highest rates of calcein uptake.

FIG. 2 shows monospecific liposomal targeting with respect to kinetics and efficacy. In contrast to previous experiments (see, FIG. 1) where cells had been incubated with liposomes for 2 hrs before harvesting and measuring, we here investigated the time kinetics of liposomal uptake, i.e. uptake of calcein at a number of time points over a 24-hour period. Although the MoDCs expressed CD14 over a broad range of membrane densities (cf. left hand graph), this phenotypic pattern was not reflected after targeting. In contrast, CD209 (DC-SIGN) targeting again revealed the highest rate of uptake; also, the patterns of antigen expression (left-hand graph) and targeting efficacy (3-h graph) were very similar. This implies that upon binding of CD209-targeted liposomes, DC-SIGN-liposome complexes apparently are almost completely internalized, thus delivering the liposomal content to intracellular compartments. This conclusion is consistent with one main function known for the CD209 receptor, i.e. uptake of larger infectious particles over a broad range of sizes including antigens, HIV, *Candida albicans*, and *Leishmania amastigotes* (e.g., Engering A, Geijtenbeek T B H, van Vliet S J, Wijers M, van Liempt B, Demaurex N, Lanzavecchia A, Fransen J, Figdor C G, Piguet V, van Kooyk Y., The dendritic cell-specific adhesion receptor DC-SIGN internalizes antigen for presentation to T cells, J Immunol. 168(5):2118-26 [2002]; Kwon D S, Gregorio G, Bitton N, Hendrickson W A, Littman D R, *DC-SIGN-mediated internalization of HIV is required for trans-enhancement of T cell infection*, Immunity 16(1):135-44 [2002]; Cambi A, Gijzen K, de Vries J M, Torensma R, Joosten B, Adema G J, Netea M G, Kullberg B J, Romani L, Figdor C G, *The C-type lectin DC-SIGN (CD209) is an antigen-uptake receptor for Candida albicans on dendritic cells*, Eur J Immunol. 33(2):532-8 [2003]; Colmenares M, Puig-Kroger A, Pello O M, Corbi A L, Rivas L, *Dendritic cell (DC)-specific intercellular adhesion molecule 3 (ICAM-3)grabbing nonintegrin (DC-SIGN, CD209), a C-type surface lectin in human DCs, is a receptor for Leishmania amastigotes*, J Biol Chem. 277(39):36766-69 [2002]).

Figure 4A:
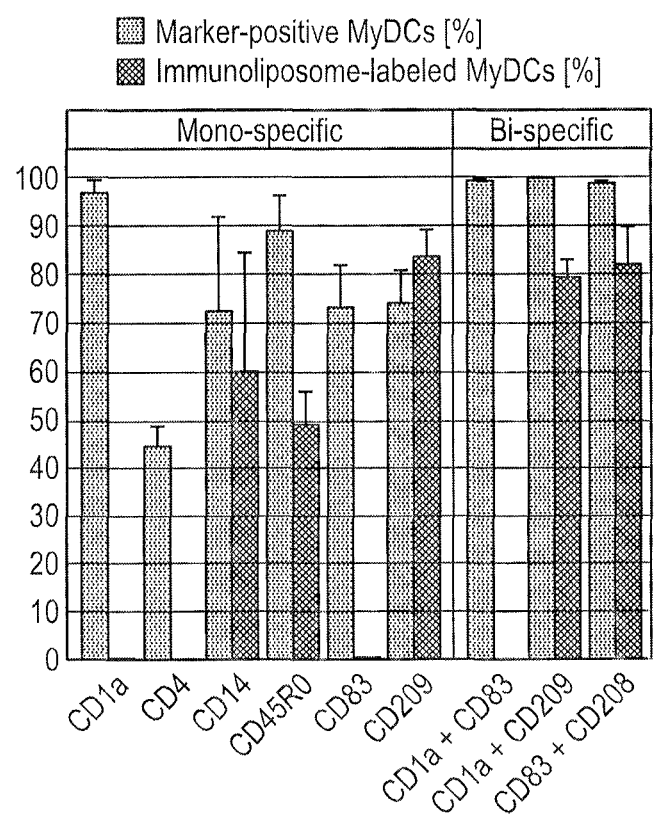
FIGS. 4A and 4B illustrates calculated values for targeting and surface binding of immunoliposomes applied to MoDCs. Provided in FIG. 4A and FIG. 4B are percentages of MoDCs expressing select markers (FITC fluorescence.
Figure 4B:
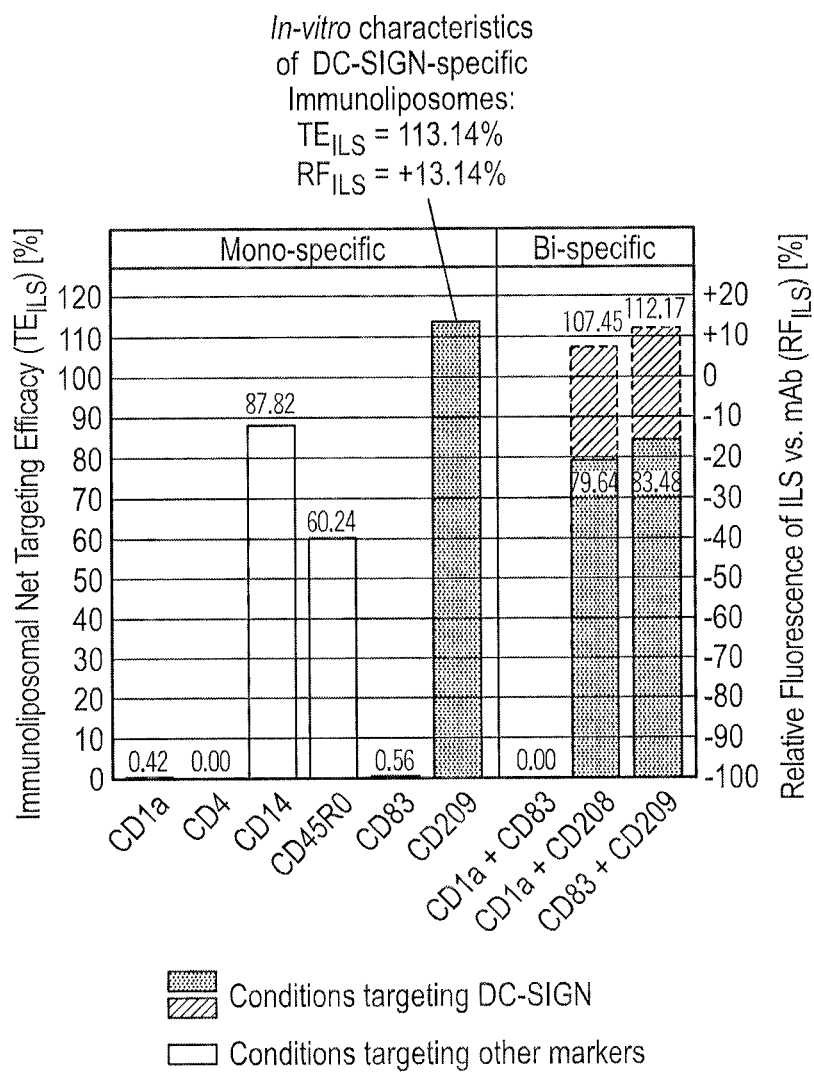

FIG. 4A (left panel) and FIG. 4B (left panel) show calculated values of targeting and surface binding of monospecific immunoliposomes applied to MoDCs; the results depicted are representative of at least three independent experiments. Provided in FIG. 4A are percentages of MoDCs expressing select markers (FITC fluorescence), and MoDCs targeted with corresponding immunoliposomes (calcein fluorescence). As FITC and calcein concentrations were equimolar in all mAb or liposome conditions, the immunoliposomal net targeting efficacy ($TE_{ILS}$) and relative fluorescence of immunoliposomes vs. mAbs ($RF_{ILS}$) could be determined (equations IV and V; FIG. 4B). Of all variants tested, mono-specific immunoliposomes targeting DC-SIGN revealed the highest $TE_{ILS}$ and were the only preparation showing a positive $RF_{ILS}$ value (indicating liposomal accumulation on or within targeted MoDCs).

The liposomal targeting efficacy of CD209-coupled liposomes was 83.31% (FIG. 4A, left panel), and the respective LS Binding/Uptake graph in FIG. 1 demonstrates for all cells a right shift (shaded curve), relative to the control peak (open curve). This indicates that 100% of the cells had been efficiently targeted, even when only faintly expressing DC-SIGN. Second, at first sight, combinations of anti-DC-SIGN liposomes with anti-CD1a or anti-CD83 liposomes (bispecific liposomes) did not effect increased uptake. However, in combinatorial onsets, antibody concentrations were only half of those employed when targeting with one antibody only. Therefore, further investigations were warranted to determine whether bispecific targeting might, indeed, enhance the targeting efficacy, when compared to monospecific targeting.

FIG. 3 illustrates liposomal targeting of DCs via two cell markers (termed "bispecific targeting"), including time dependency of the targeting efficacy over a 24-h period. Bispecific targeting was carried out with all 2-member combinations, or permutations, of CD4, CD45RO and CD209. As in FIG. 2, best results were, here again, obtained upon 3-h incubation of cells with targeted liposomes.

FIG. 3A shows results for the combination of anti-CD4 plus anti-CD45RO targeting ligands. Irrespective of the incubation time, when compared to the experiment shown in FIG. 2, a subtractive effect on liposomal uptake was obtained. Combination of anti-CD4- and anti-CD45RO-specific targeting, therefore, did not appear to support enhanced uptake by a double-positive cell subset, e.g. the resting T-memory cell population residing in lymphoid organs. A similar result was observed for liposomes bearing the combination of anti-CD209 plus anti-CD45R0 targeting ligands (FIG. 3C).

FIG. 3B shows results for the combination of anti-CD4 plus anti-CD209 targeting ligands. When compared to the experiment shown in FIG. 2, there was an additive effect on liposomal uptake as a result of the combination of targeting ligands Of note, the abscissa in FIG. 3B shows liposomal uptake as a logarithmic increase in fluorescence. Therefore, the improvement of uptake by combined targeting of CD4 and CD209 was at least by a factor of 2 and thus, in accordance with the invention, liposomal targeting dendritic cells employing a combination of anti-CD4 and anti-CD209 targeting ligands can be a useful option, for example, in treating HIV disease. Adipocytes, another HIV reservoir, can also be targeted by targeting via CD4 and CD45 (e.g., Hazan, U. et al., *Human adipose cells express CD4, CXCR4, and CCR5 receptors: a new target cell type for the immunodeficiency virus-1? FASEB J.* 16, 1254-1256 [2002;] Erratum in: FASEB J. 16:4 (2000); Kannisto, K. et al., *Expression of adipogenic transcription factors, peroxisome proliferator-activated receptor γ co-activator 1, IL-6 and CD45 in subcutaneous adipose tissue in lipodystrophy associated with highly active antiretroviral therapy, AIDS* 17, 1753-1762 [2003]).

At half-saturating concentration in the bi-specific onsets, targeting for CD209 seemed to compensate for much of the lacking targeting efficacy of the CD1a- or CD83-directed variants (B; bi-specific: solid-lined bars). However, comparison between the mono-specific and bi-specific onsets for CD209 (FIG. 4A) revealed that, even at half-saturating conditions, all cells expressing DC-SIGN had been labeled, which resulted in a $TE_{ILS}$ of 107.46% for CD1a/CD209 and a $TE_{ILS}$ of 112.17% for CD83/CD209 (FIG. 4B; bi-specific: dashed bars; approximations due to the saturating anti-CD209 reference condition in FIG. 4A). Both the results for saturating and non-saturating CD209-specific liposomes suggest for MyDCs a limiting uptake kinetic at $TE_{ILS}$ about 110%.

In FIG. 4B (right panel), a net targeting efficiency with a positive (+) value indicates that the percentage of cells targeted efficaciously was higher than the percentage recognized by antibody only; negative (−) values indicate less efficient targeting than with antibody; a value of −100% indicates that no cells at all have been targeted. All values refer to 3-hour co-incubation of cells and targeted liposomes. The three best targeting conditions were CD209>CD83+CD209>CD1a+CD209. Targeting efficacy for bispecific immunoliposomes targeting CD4+CD45R0 was 58.54%; targeting efficacy for bispecific immunoliposomes targeting CD4+CD209 was 68.74%; targeting efficacy for bispecific immunoliposomes targeting CD45R0+CD209 was 62.21%.

The data presented herein indicate that a DC-SIGN-targeted system can target different HIV reservoir populations, i.e., myeloid dendritic cells and macrophage subsets, for delivering HIV-inhibiting compounds of any or all types currently known. In accordance with the present invention, these reservoir populations can be targeted for integrating DC-SIGN-attached viruses for successive generation of immunity as well as to remove virus from the cells' surfaces, and mother-to-child virus transfer during pregnancy can be prevented. DC-SIGN is strongly expressed by mucosal and skin types of dendritic cells in humans and macaques. (Geijtenbeek, T B et al., *DC-SIGN: a novel HIV receptor on DCs that mediates HIV-1 transmission*, Curr Top Microbiol Immunol. 2003; 276:31-54 [2003]; Yu Kimata M T et al., *Capture and transfer of simian immunodeficiency virus by macaque dendritic cells is enhanced by DC-SIGN*, J Virol. 76(23):11827-36 [2002]). Thus, treating HIV-infected individuals with DC-SIGN-targeted liposomes, in accordance with the present invention, offers the benefit of actively targeting the first cell population infected and affected in the etiology of HIV disease.

DC-SIGN is further expressed by dendritic and other cells located within certain placental anatomic structures. (E.g., Soilleux E J et al, *Placental expression of DC-SIGN may mediate intrauterine vertical transmission of HIV*, J Pathol. 195(5):586-92 [2001]; Soilleux E J, Coleman N, Transplacental transmission of HIV: a potential role for HIV binding lectins, Int J Biochem Cell Biol. 2003 March; 35(3):283-7 [2003]; Kammerer U et al., *Unique appearance of proliferating antigen presenting cells expressing DC-SIGN (CD209) in the decidua of early human pregnancy*, Am J Pathol. 162(3):887-96 [2003]). Thus, if administered by intravenous, subcutaneous or direct in-utero application, the inventive method offers the benefit of targeting those cells that apparently play a major role in mother-to-child HIV transfer, also termed vertical transmission.

Example 3. Fluorescence-Microscopic Uptake Studies

After infection with HIV-1, intracytoplasmic compartments with accumulated infectious virus are demonstrable in both immature and mature MyDCs (Frank, I et al., *Infectious and whole inactivated simian immunodeficiency viruses interact similarly with primate dendritic cells (DCs): differential intracellular fee of virions in mature and immature DCs*, J Virol 76:2936-51 [2002]). Therefore for comparison, immature or mature MoDCs were incubated for 3, 4 or 5 h at 37° C. with anti-CD209-labeled liposomes (each at n=3). The cells were then harvested as described above and gently pipetted to dissociate homotypic clusters (as controlled by phase microscopy). Pelleted single cells were successively dissolved in 100 μl of ProLong antifade mounting ine,dium to which was added 5 μM of the positively charged AT-binding DNA dye, 4',6-diamidino-2-phenylindole (DAPI) (both from Molecular Probes, Eugene, Oreg., USA). Fifty μl of each preparation were transferred to poly-L-lysine-coated slides (Labscientific, Livingston, N.Y., USA), cover-slipped, sealed and kept in the dark for at least 15 min before being viewed. Sifting through about 100 cells per preparation, MoDCs were then screened with a Zeiss Axioskop microscope (Carl Zeiss, Thornwood, N.Y., USA) for surface and intracellular fluorescence of calcein (green) and DNA/nuclei (blue). Photomicrographic tomographies of MyDCs displaying representative staining were performed at 0.5-μm steps, achieving 27-35 serial sections per cell (thus implying a range in diameter for MyDCs of 13.5-17.5 μm at n=12). Digital photography was carried out with an ORCA-1 CCD camera (Hanaamatsu, Bridgewater, N.J., USA). Photographic processing, merging of green and blue fluorescence, as well as microtomography linking to generate film clips covering MyDCs in optical depth was performed with the Northern Elite V.6.0 software package (Empix Imaging, Cheek Towaga, N.Y., USA). Dead cells were excluded from the evaluation by nuclear staining with propidium iodide as well as by their extremely bright nuclear DAPI staining.

Immunoliposomes carrying mAb MOPC-21/P3 were taken as negative controls; positive controls employed anti-CD209 mAb×FITC.

Figure 5:
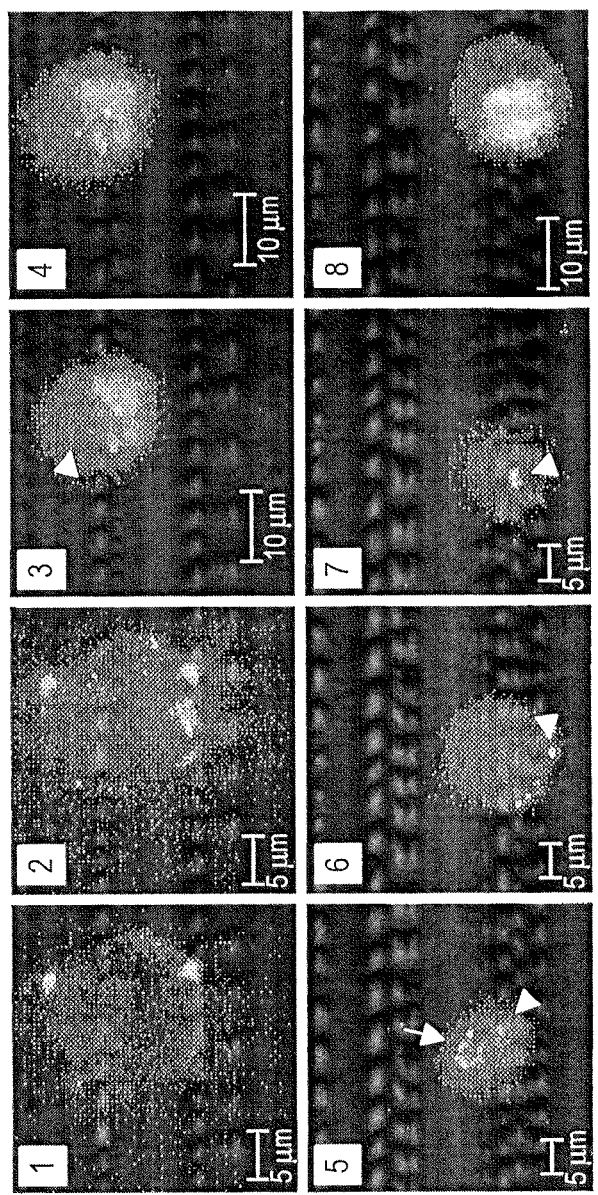
FIG. 5 shows surface binding vs. internalization of targeted liposomes as determined by fluorescence microscopy. Original magnifications: ×1000 (panels 1 and 2) and ×400 (panels 3-8).

FIG. 5 illustrates surface binding vs. internalization of targeted liposomes determined by fluorescence microscopy as described above. For discerning intracellular from outshining membrane fluorescence, we then, at steps of 0.5 µm, photographed 27 to 35 microtomographies per MoDC body. After 3-h incubation with CD209-specific liposomes (corresponding to the CD209 condition in FIG. 4B), green calcein labeling was seen only on the cell surface and was mainly confined to larger DC-SIGN-rich lipid rafts (FIG. 5, panel 1; depicting the median optical section). An overlay of all serial sections of the same cell reveals another superimposed DC-SIGN lipid raft in the lower foreground, and some scattered fluorescence corresponding to the size of liposomes (FIG. 5, panel 2). However, after 5-h incubation, liposomally entrapped calcein had been completely internalized. In all of about 100 MoDCs examined per condition, the cells revealed both diffuse and concentrated areas of intracellular fluorescence (FIG. 5, panels 3-8). Importantly, areas displaying much lower fluorescence intensity (FIG. 5, panel 3; arrowhead) were always identified as nuclei, clearly proving intracellular delivery of the tracer compound (FIG. 5, panel 4; depicting the cell shown in FIG. 5, panel 3, merged with blue nuclear DAPI staining). Occasionally, some liposomal binding was still seen in CD209-rich surface rafts (FIG. 5, panel 5; arrow) while most calcein was internalized (FIG. 5, panel 5; arrowhead). At this time, compartments highly enriched in calcein were seen in all MoDCs (FIG. 5, panel 6; arrowhead), and about one quarter of them revealed prominent perinuclear fluorescence (FIG. 5, panel 7). Depending on the amount of uptake, this area sometimes covered a large portion of the extranuclear space (FIG. 5, panel 8). While results obtained with immature MyDCs incubated under the same conditions were essentially identical, intracellular liposome/calcein uptake was seen already after 4-h incubation (not separately shown). Quenching of extracellular fluorescence with trypan blue completely blocked out fluorescence when cells had been incubated for 3 h, but had no effect after 5-h incubation, thereby confirming the results depicted in FIG. 5.

Negative controls did not show surface binding or uptake, while positive controls were very rapidly bound and internalized (not shown). When adding DC-SIGN-specific FITC-conjugated mAb to lipopolysaccharide-matured human MyDCs, Schjetne et al. have shown that it is located extracellularly 15 min later, and intracellularly after 45 min (Schjetne K W et al., *A mouse Cx-specific T cell clone indicates that DC-SIGN is an efficient target for antibody-mediated delivery of T cell epitopes for MHC class II presentation*, Int Immunol 14:1423-30 [2002]). Employing DCs generated by a slightly different protocol, the results in our positive control with HI C-labeled anti-DC-SIGN mAb were similar.

In contrast, intracellular uptake of the larger, targeted liposomes took longer, up to 5 hours, depending on the MoDCs' stage of maturity. While these results imply that the size of DC-SIGN-bound particles inversely correlates with the time required for cellular uptake, the size of the liposomes employed herein (with an average diameter of about 150 nm) does not preclude their uptake. Therefore, by replacing the tracer compound with suitable drugs, these liposomes, in accordance with the invention, are valuable DC-specific targeting vehicles. This reasoning is further supported by the consistently high surface expression of CD209 (DC-SIGN) with, for example, at least $1\times10^5$ molecules per immature MoDC, thus furnishing a very reliable target (Baribaud F et al., *Quantitative expression and virus transmission analysis of DC-SIGN on monocyte-derived dendritic cells*, J Virol 76:9135-42 [2002]). Importantly, the targeting efficacy we demonstrated was achieved in the presence of mannan- or mannose-binding lectin (MBL) which very likely—as a liver-derived substance (Downing, I et al., Immature dendritic cells possess a sugar-sensitive receptor for human mannan-binding lectin, Immunology 109:360-4 [2003])—constitutes a component of the small amount of fetal bovine serum employed during culture and incubation. In any event, it has recently been shown that MBL is even autologously secreted by immature human MoDCs (Downing I et al., *Immature dendritic cells possess a sugar-sensitive receptor for human mannan-binding lectin*, Immunology 2003; 109:360-4 [2003]). Furthermore, MBL, via its own C-type lectin domain, can prevent HIV-1 from binding to DC-SIGN (Spear G T et al., Inhibition of DC-SIGN-mediated trans infection of T cells by mannose-binding lectin, Immunology 2003; 110:80-5 [2003]). Therefore, soluble MBL (and perhaps other unidentified molecules displaying similar characteristics) did not prevent the inventive DC-SIGN-specific liposomes from interacting with the membrane-bound C-type lectin.

By employing a liposomally entrapped tracer, calcein, we flow-cytometrically and mathematically demonstrated a superior targeting efficacy for DC-SIGN, as compared with select other MyDC markers (CD1a, CD4, CD45RO, CD83). Fluorescence microscopy further revealed time-dependent surface binding and intracellular uptake of DC-SIGN-specific liposomes by both immature and mature MyDCs. The net targeting efficacy we found for DC-SIGN-specific iramunoliposomes, as well as the fluoromicrographic uptake studies, clearly reveal efficient binding, internalization and intracellular compound delivery. We have shown that DC-SIGN-targeted immunoliposornes (i.e., including targeting ligand that specifically binds CD209) deliver their contents both to immature and mature MyDCs, and that, in addition to cytoplasmatic distribution, their contents strongly accumulate in discrete intracellular compartments (FIG. 5), or endosomes, respectively. These observations, together with the fact that HIV-1 and the liposomes administered are comparable in size, enable the inventive delivery system to reach exactly the same compartments where highly infectious HIV-1 is stored and rescued from any systemic attack until being released to infect further Th cells. Suitable immunoliposomally delivered agents, in accordance with the present invention, will thus reach an important sanctuary that is not as yet addressed by any therapeutic strategy. Another important benefit is that, due to the fact that these liposomes are retained on the surface of MyDCs for prolonged times, Th cells interacting with DCs within lymphoid organs and tissues in the course of antigen-specific stimulation can also be reached therapeutically by this strategy (Gieseler R K, Marquitan G, Hahn M J, Perdon L A, Driessen W H P, Sullivan S M, Scolaro M J, *DC-SIGN-specific liposomal targeting and selective intracellular compound delivery to human myeloid dendritic cells: implications for HIV disease*, Scand J Immunol; 59:415-24 [2004]; Marquitan G, Gieseler R K, Driessen W H P, Perdon L A, Hahn M J, Wader T, Sullivan S M, Scolaro M J, *Intracellular compound delivery to human monocyte-derived dendritic cells by immunoliposomal targeting of the C-type lectin DC-SIGN*. MACS & MORE, in press [2004]).

The invention claimed is:

1. A method of preferentially delivering a drug to an immune cell being affected with, or susceptible to infection with, an infectious agent, comprising:
 administering to a mammalian subject a lipid-drug complex comprising:
 a) at least one drug; and
 b) a lipid shell comprising on its outer surface targeting ligands that specifically bind to the CD4 and CD45R0 marker combination co-expressed on the surface of the immune cell,
 wherein said immune cell is a T helper memory cell, and
 wherein said drug is a carbohydrate binding protein, wherein the carbohydrate-binding protein is IDS-30 (Hox alpha) extract of the stinging nettle, rhizome-derived *Urtica dioica* agglutinin (UDA) derived from *Urtica dioica*, or *Myrianthus holstii* lectin (MHL) derived from *Myrianthus holstii,*
 and wherein the targeting ligands are monoclonal antibodies or F(ab) or $F(ab)_2$ fragments thereof.

2. The method of claim 1, wherein the infectious agent is a virus, a bacterium, a fungus, a protozoan, or a prion.

3. The method of claim 2, wherein the virus is selected from the group consisting of HIV, HSV, EBV, CMV, Ebola and Marburg virus, HAV, HBV, HCV and HPV.

4. The method of claim 1, wherein the lipid-drug complex is a liposome-drug complex.

5. The method of claim 1, wherein the lipid-drug complex further comprises one or more secondary drugs.

6. The method of claim 1, wherein administering is by a subcutaneous, an intradermal, an intraperitoneal, an intravenous, a transvascular, or a parenteral route.

7. The method of claim 1, wherein the outer surface of the lipid shell further comprises a *Staphylococcus aureus* protein A adapted for specifically binding IgG.

8. The method of claim 7, wherein the targeting ligands are monoclonal or polyclonal antibodies specifically bound by the *Staphylococcus aureus* protein A.

* * * * *